(12) United States Patent
Hendricks et al.

(10) Patent No.: US 9,050,454 B2
(45) Date of Patent: Jun. 9, 2015

(54) ELECTRICALLY CONDUCTIVE AND MECHANICALLY SUPPORTIVE POLYMER MATERIALS FOR BIOMEDICAL LEADS

(71) Applicant: Biotectix, LLC, Boston, MA (US)

(72) Inventors: Jeffrey Hendricks, Ann Arbor, MI (US); Sarah Richardson-Burns, Ann Arbor, MI (US); Amir Tehrani, San Francisco, CA (US)

(73) Assignee: BIOTECTIX, LLC, Boston, MA (US)

( * ) Notice: Subject to any disclaimer, the term of this patent is extended or adjusted under 35 U.S.C. 154(b) by 0 days.

(21) Appl. No.: 14/071,065

(22) Filed: Nov. 4, 2013

(65) Prior Publication Data

US 2014/0058489 A1   Feb. 27, 2014

Related U.S. Application Data

(62) Division of application No. 13/044,492, filed on Mar. 9, 2011, now Pat. No. 8,577,476.

(60) Provisional application No. 61/312,241, filed on Mar. 9, 2010.

(51) Int. Cl.
  *A61N 1/06* (2006.01)
  *A61N 1/05* (2006.01)

(52) U.S. Cl.
  CPC . *A61N 1/05* (2013.01); *A61N 1/056* (2013.01)

(58) Field of Classification Search
  USPC ........................................................ 607/116
  See application file for complete search history.

(56) References Cited

U.S. PATENT DOCUMENTS

| | | | |
|---|---|---|---|
| 4,027,677 A | 6/1977 | Schulman et al. |
| 4,033,355 A | 7/1977 | Amundson |
| 4,056,302 A | 11/1977 | Braun et al. |
| 4,396,409 A | 8/1983 | Bailey et al. |
| 5,246,014 A | 9/1993 | Williams et al. |
| 5,300,108 A | 4/1994 | Rebell et al. |
| 5,522,872 A | 6/1996 | Hoff |
| 5,554,176 A | 9/1996 | Maddison et al. |
| 5,944,715 A | 8/1999 | Goble et al. |
| 6,018,683 A | 1/2000 | Verness et al. |
| 6,061,598 A | 5/2000 | Verness et al. |
| 6,119,042 A | 9/2000 | Verness et al. |
| 6,285,910 B1 | 9/2001 | Verness et al. |
| 6,374,141 B1 | 4/2002 | Sass |
| 6,546,292 B1 | 4/2003 | Steinhaus et al. |
| 6,564,107 B1 | 5/2003 | Bodner et al. |
| 6,701,191 B2 | 3/2004 | Schell |
| 6,717,056 B2 | 4/2004 | Rivelli et al. |

(Continued)

FOREIGN PATENT DOCUMENTS

JP   09-192239 A   7/1997
JP   2007-500038 A   1/2007

*Primary Examiner* — Paula J Stice
(74) *Attorney, Agent, or Firm* — Senniger Powers LLP

(57) ABSTRACT

An implantable medical lead connecting to a device header of a medical apparatus and having an electrode, a conductor, and a conductive polymer layer formed on at least a portion of the medical lead. An insulative sheath surrounds the conductive polymer layer for electrical insulation. The conductive polymer layer and insulative sheath maintain mechanical and electrical continuity of the lead in the event of fracture. The conductive polymer layer is composed of conductive polymers and may contain one or more dopants for improving electrical characteristics, mechanical characteristics, and processability.

34 Claims, 35 Drawing Sheets

(56) References Cited

U.S. PATENT DOCUMENTS

| | | |
|---|---|---|
| 6,785,576 B2 | 8/2004 | Verness |
| 7,031,777 B2 | 4/2006 | Hine et al. |
| 7,289,846 B2 | 10/2007 | Shoberg et al. |
| 7,292,894 B2 | 11/2007 | Belden |
| 7,313,445 B2 | 12/2007 | McVenes et al. |
| 7,337,009 B2 | 2/2008 | Schell |
| 7,660,635 B1 | 2/2010 | Verness et al. |
| 7,904,174 B2 | 3/2011 | Hammill et al. |
| 8,005,526 B2 * | 8/2011 | Martin et al. ............ 600/372 |
| 2002/0077685 A1 * | 6/2002 | Sundquist et al. ......... 607/116 |
| 2002/0099430 A1 | 7/2002 | Verness |
| 2003/0040787 A1 | 2/2003 | Flynn et al. |
| 2004/0064174 A1 | 4/2004 | Belden |
| 2004/0068313 A1 | 4/2004 | Jenney et al. |
| 2004/0102813 A1 | 5/2004 | Kranz et al. |
| 2005/0096719 A1 | 5/2005 | Hammill et al. |
| 2005/0240252 A1 * | 10/2005 | Boser et al. ............... 607/116 |
| 2006/0089691 A1 | 4/2006 | Kaplan et al. |
| 2006/0265039 A1 * | 11/2006 | Bartic et al. .............. 607/116 |
| 2007/0225785 A1 * | 9/2007 | Park et al. ................. 607/116 |
| 2007/0255378 A1 | 11/2007 | Polkinghorne et al. |
| 2008/0046049 A1 * | 2/2008 | Skubitz et al. ............ 607/115 |
| 2008/0152984 A1 | 6/2008 | Nakanishi et al. |
| 2008/0269857 A1 | 10/2008 | Cross et al. |
| 2009/0299446 A1 | 12/2009 | Lovoi et al. |
| 2010/0145447 A1 | 6/2010 | Jia et al. |
| 2010/0148635 A1 | 6/2010 | Kwon et al. |
| 2010/0152794 A1 | 6/2010 | Radivojevic et al. |
| 2011/0046706 A1 | 2/2011 | McDonald et al. |
| 2012/0277840 A1 * | 11/2012 | Flach et al. .............. 607/119 |

* cited by examiner

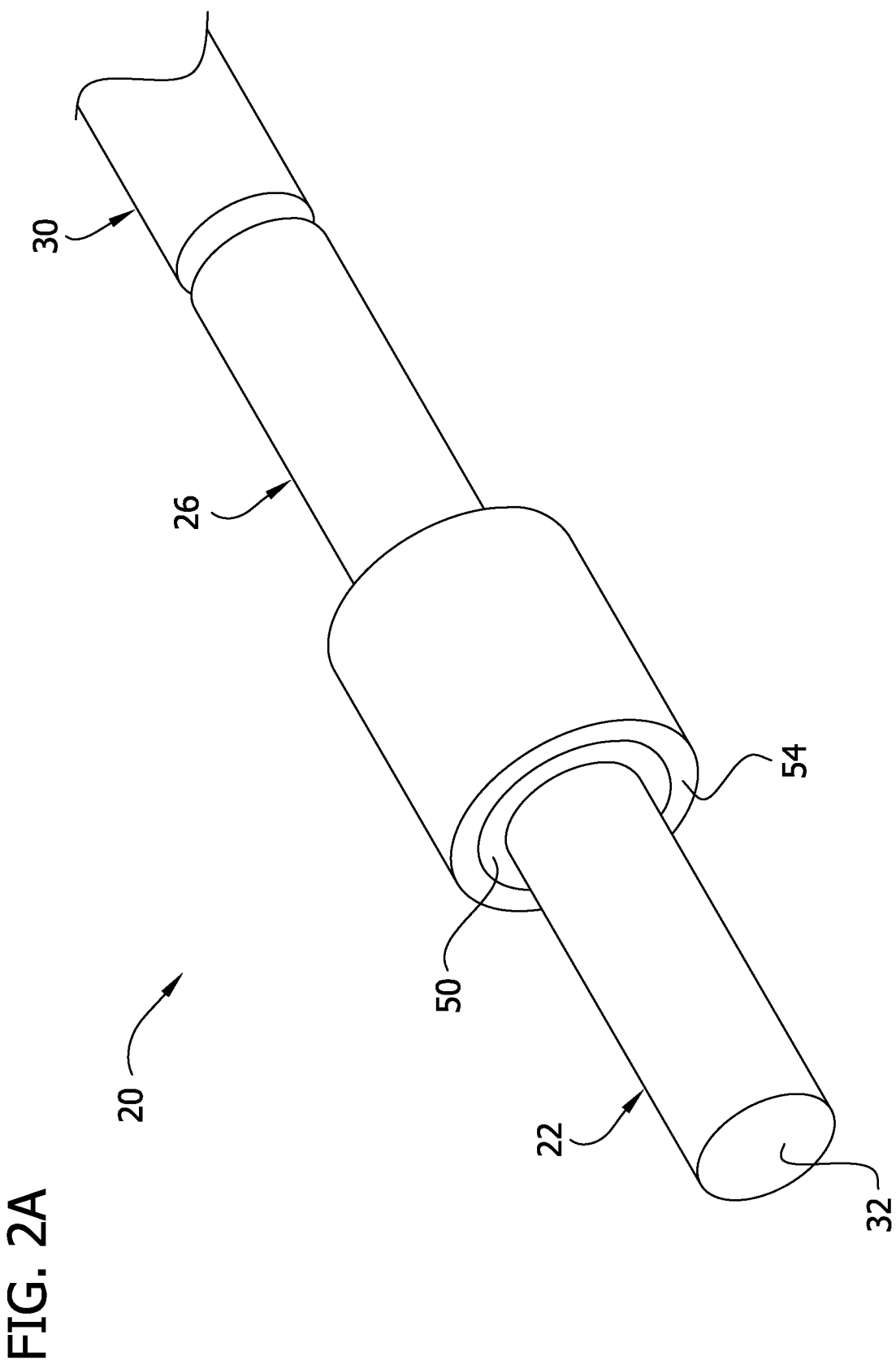

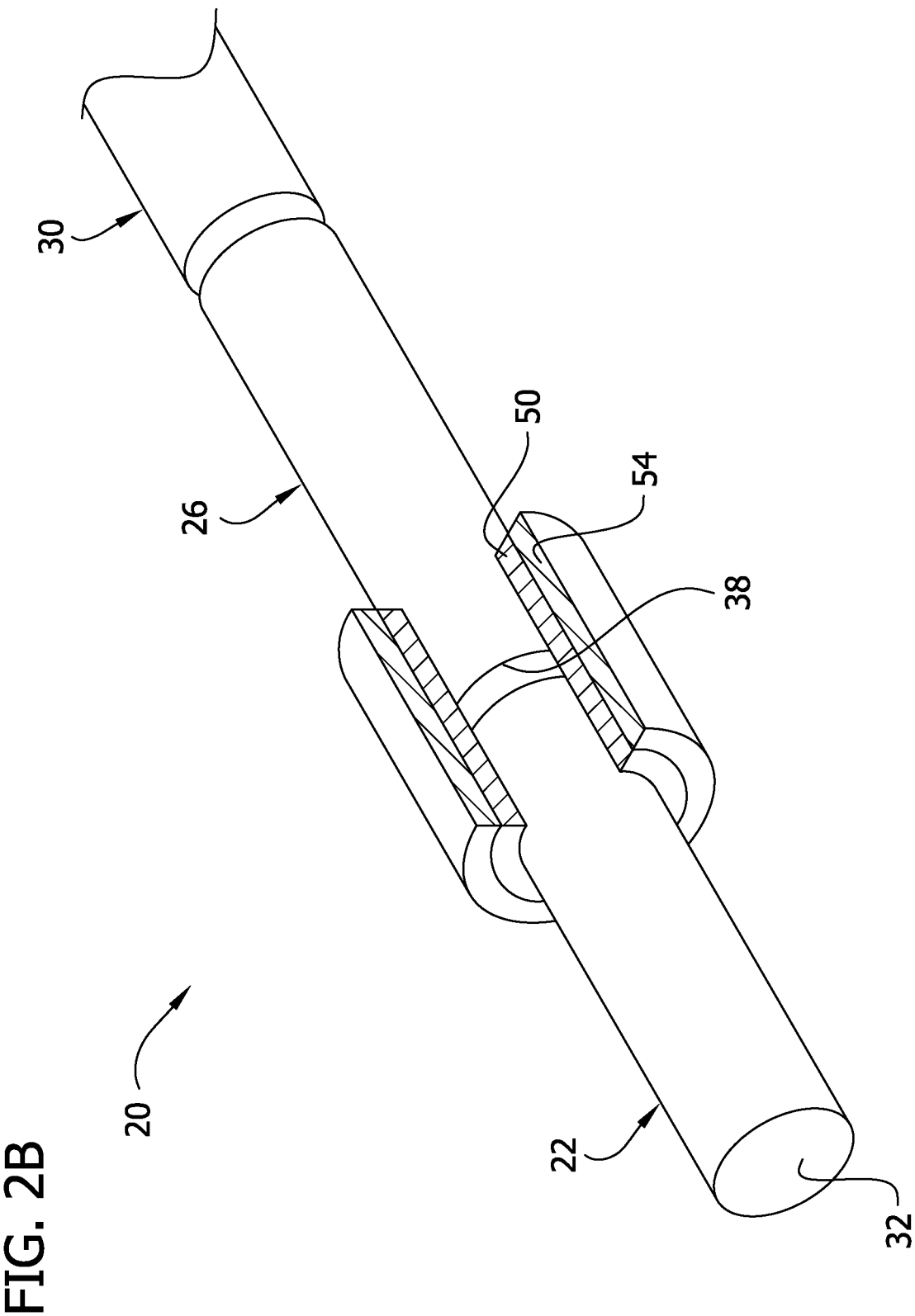

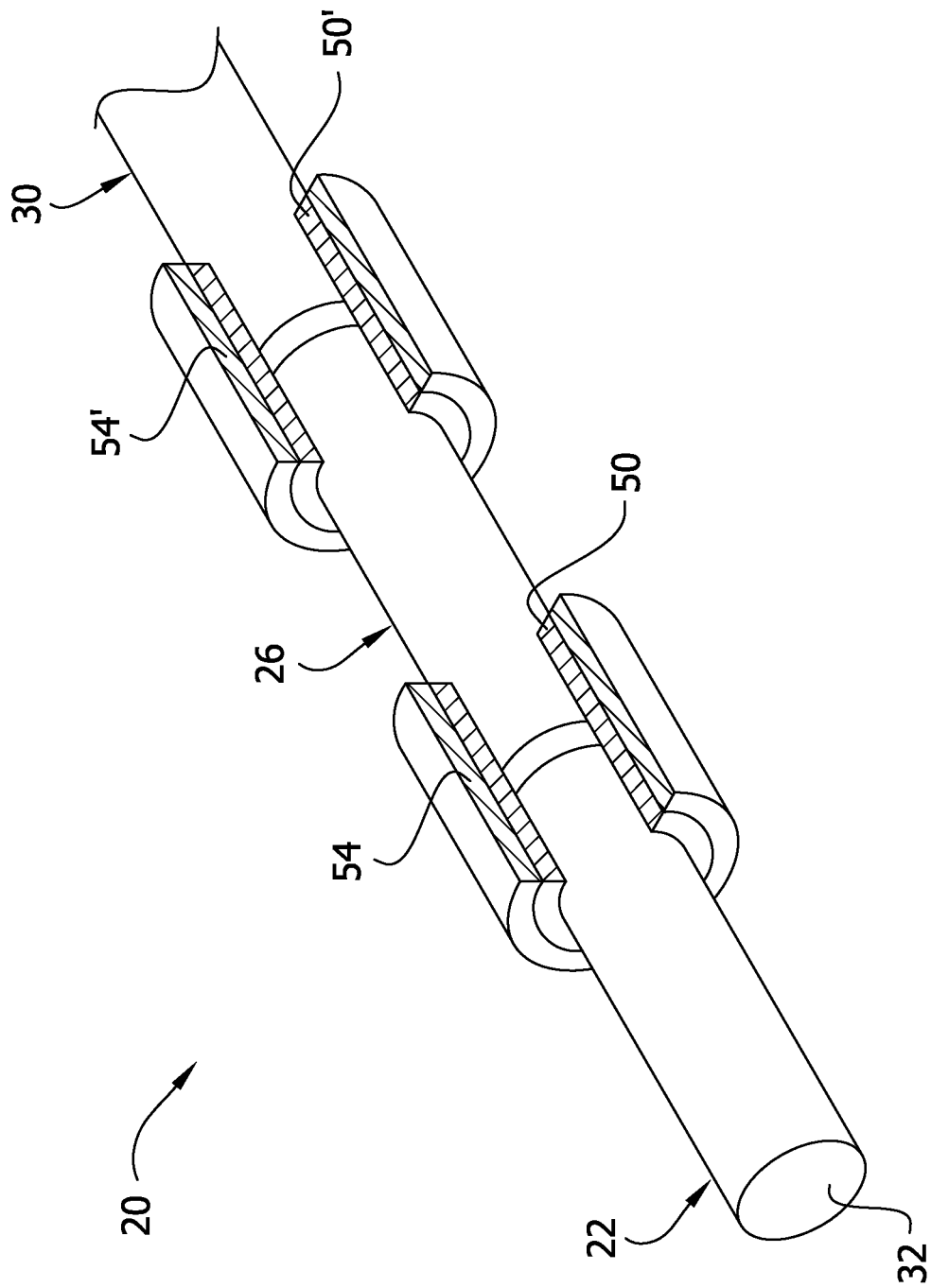

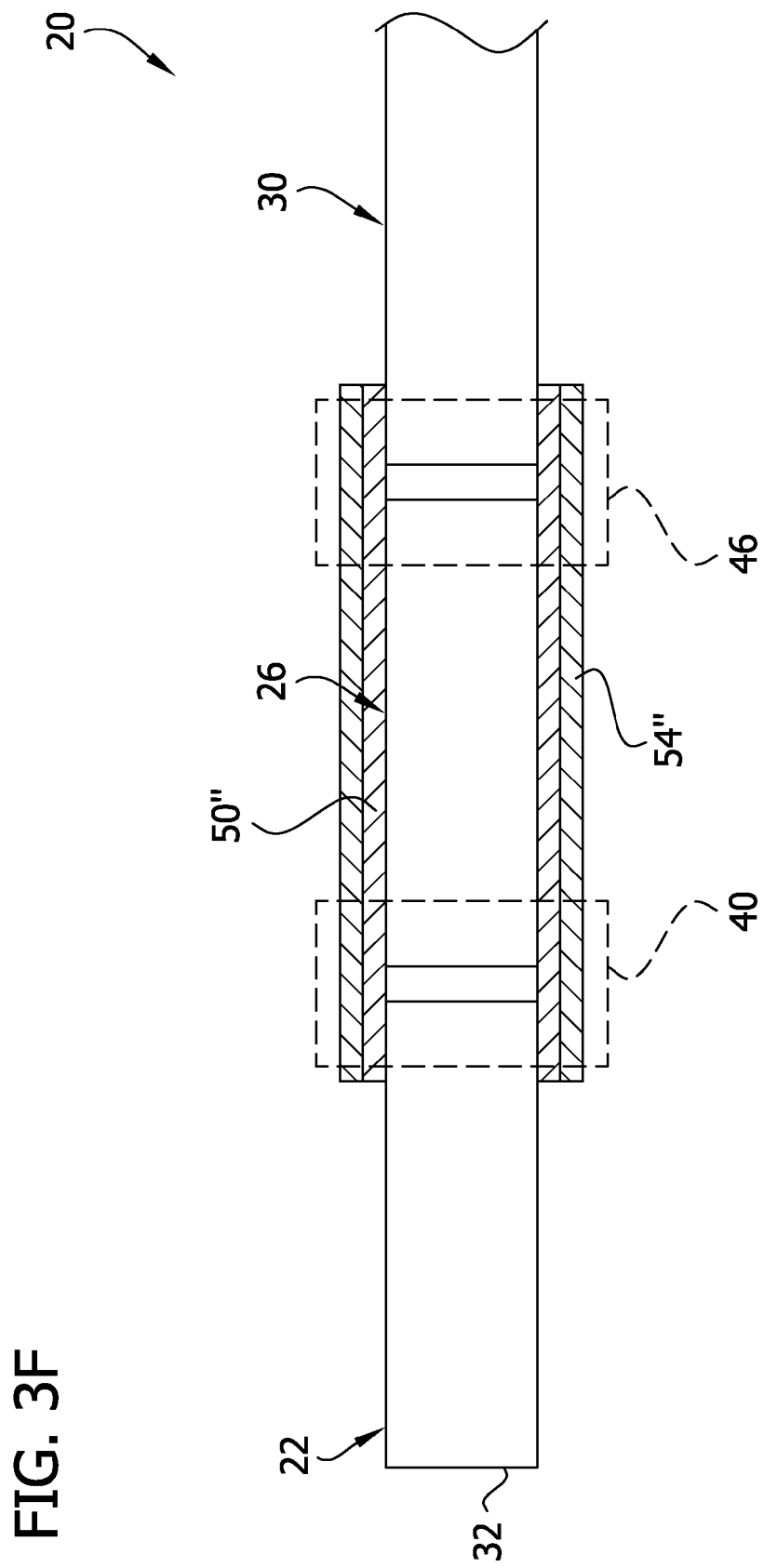

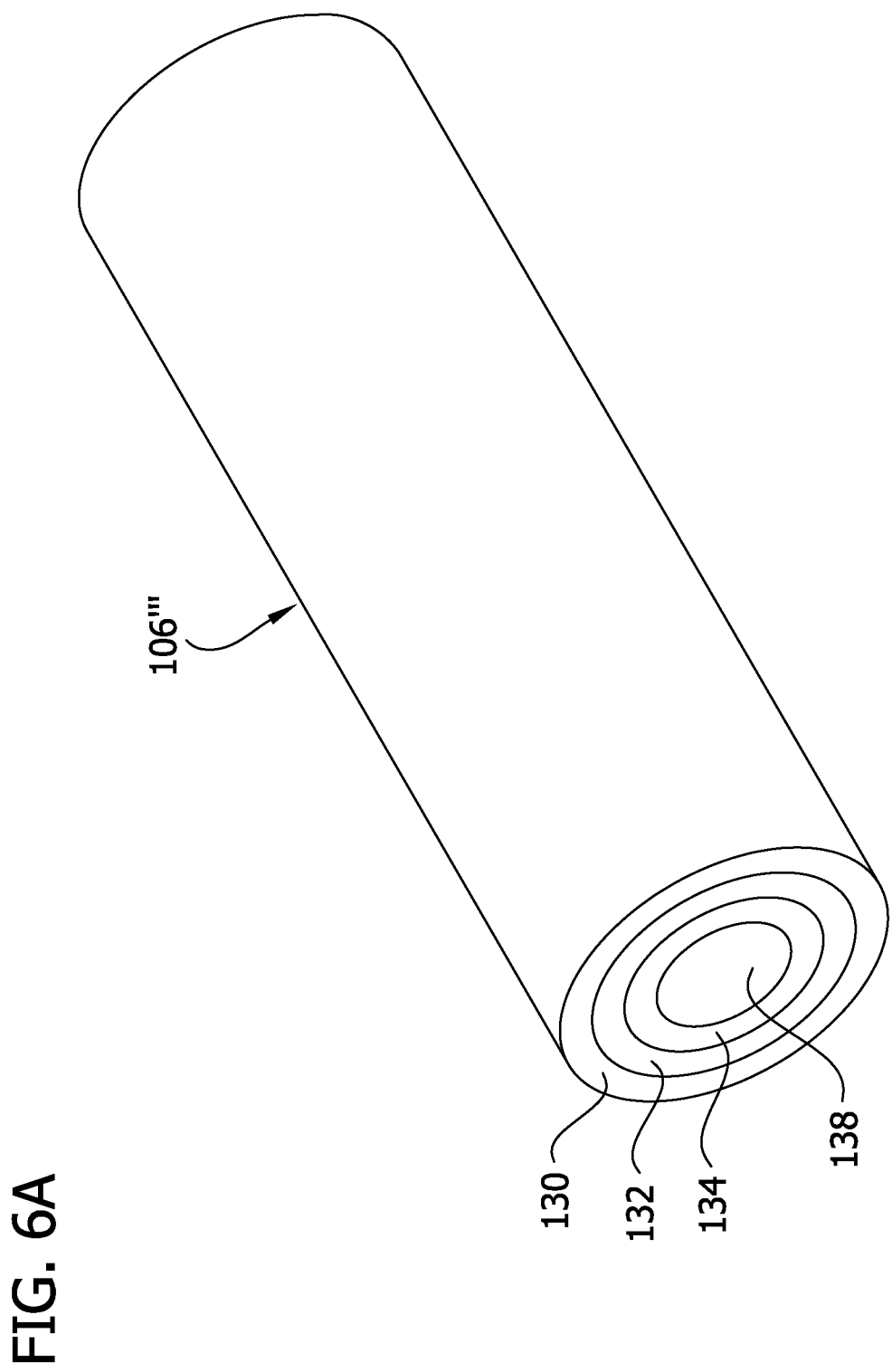

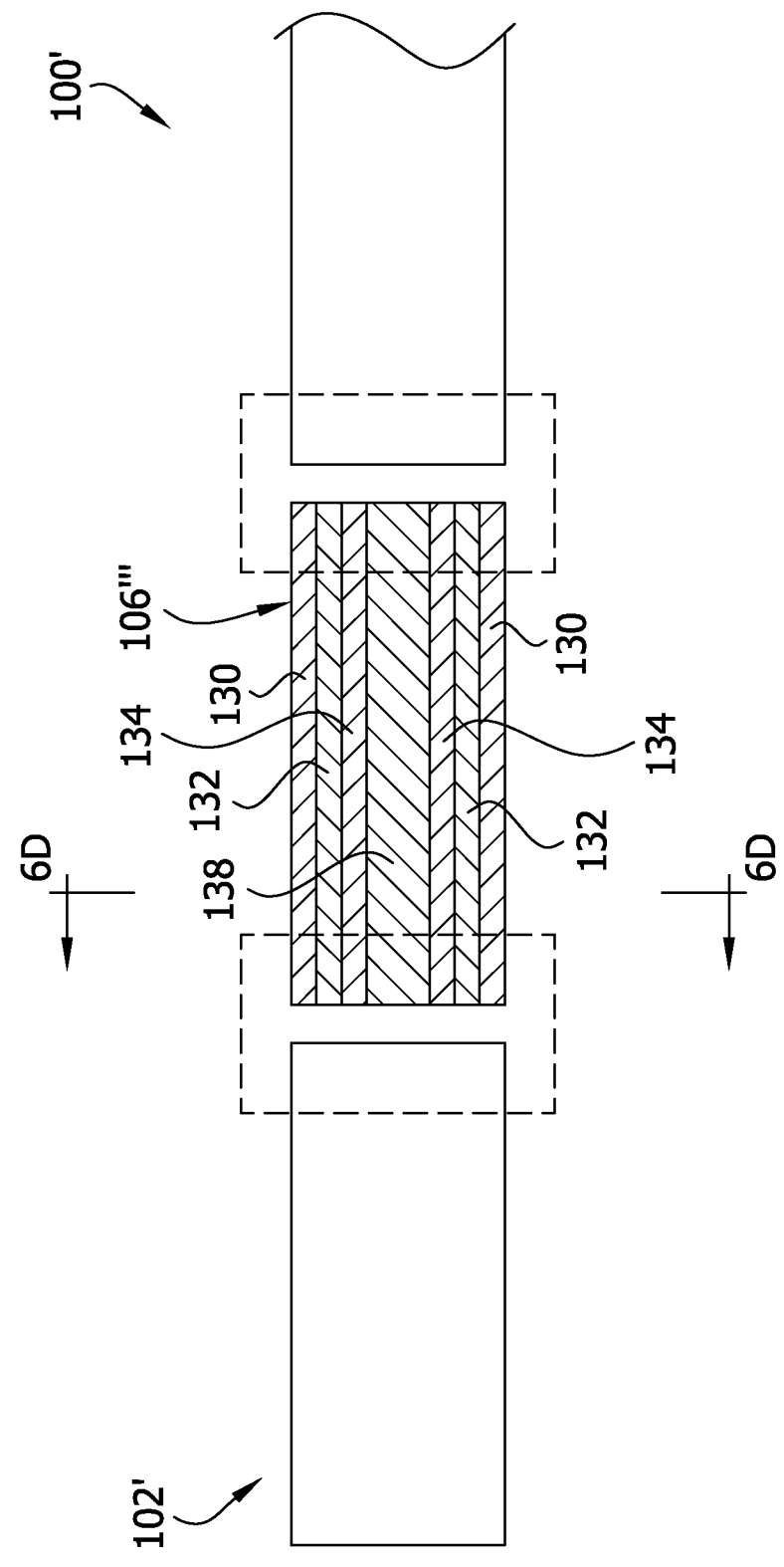

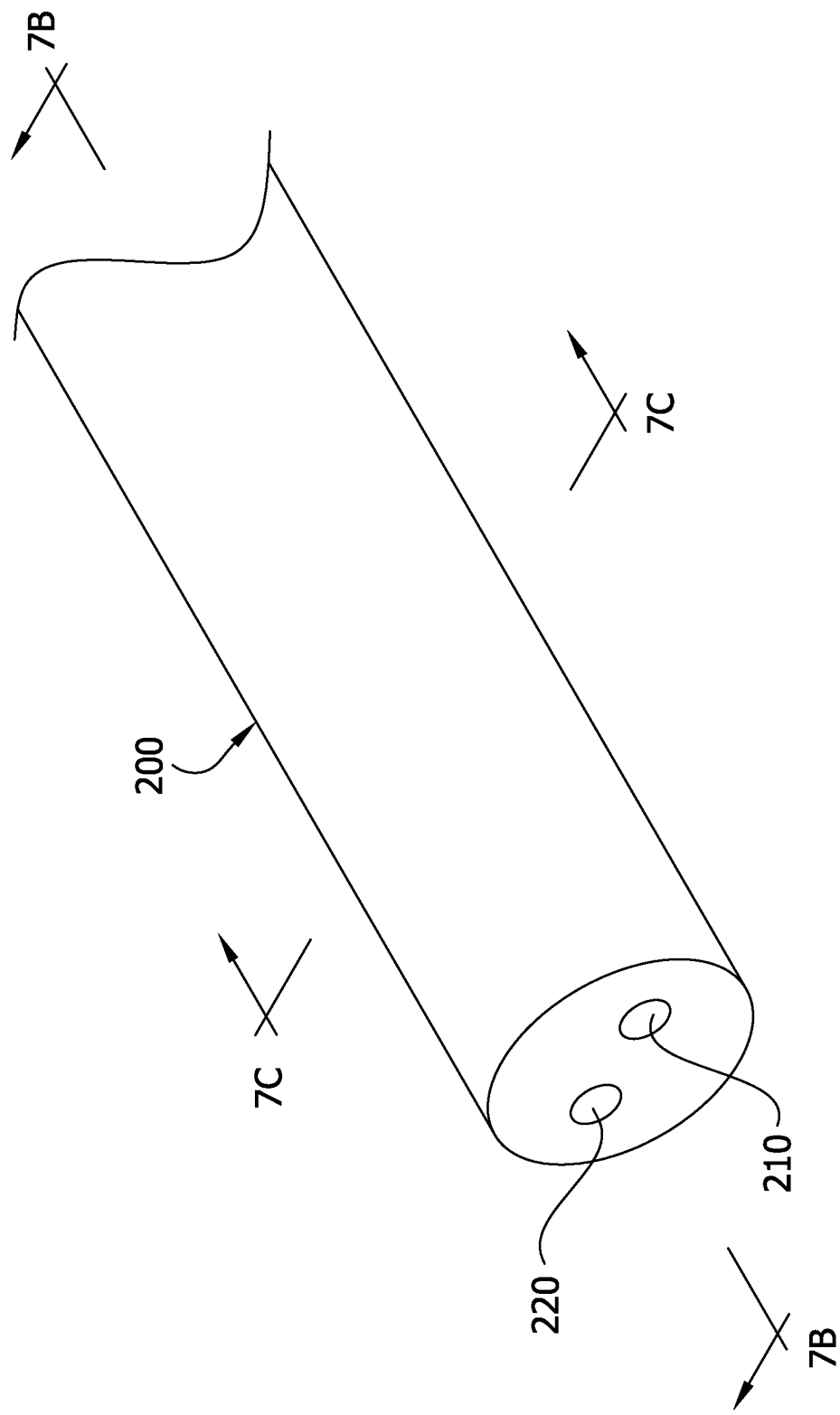

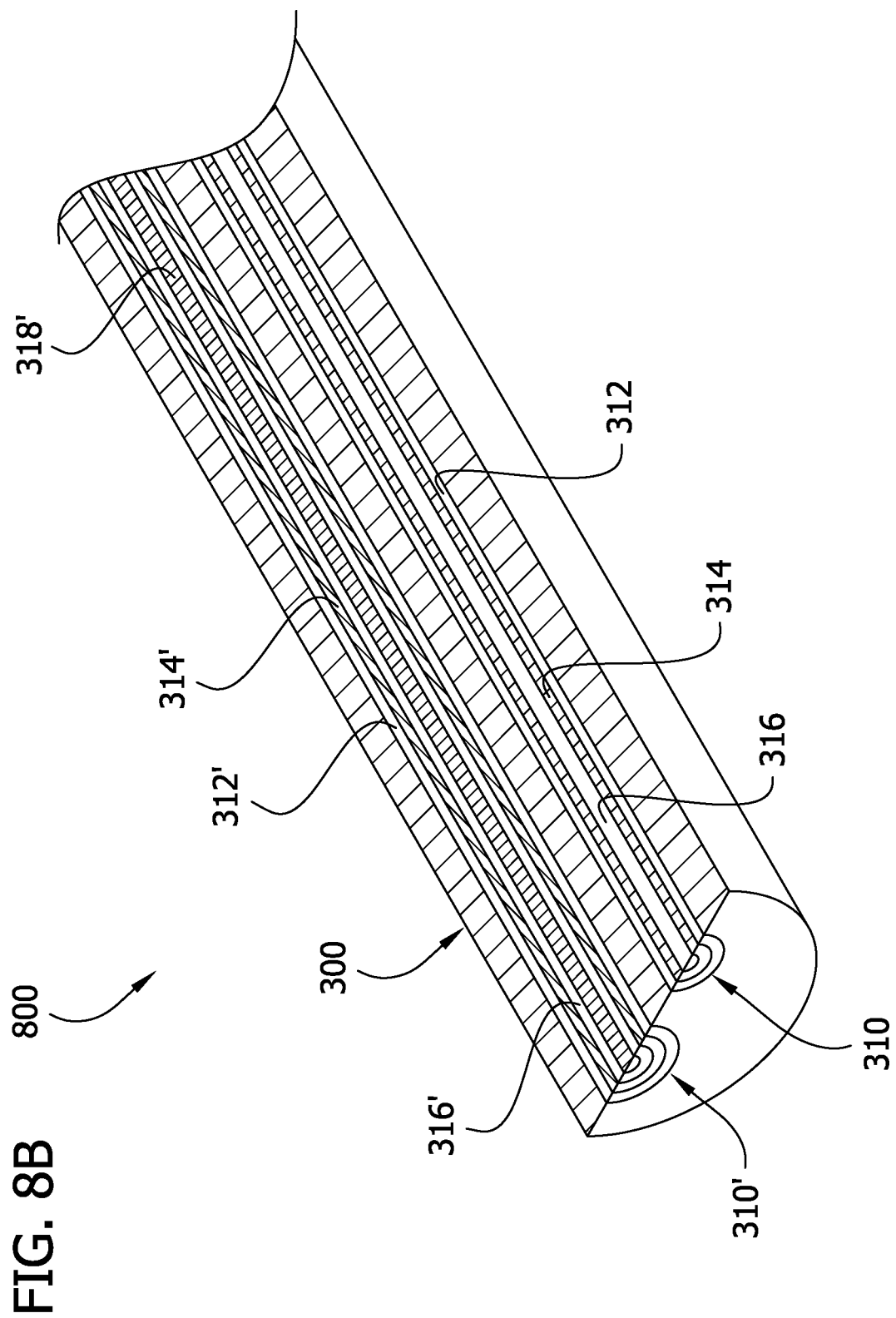

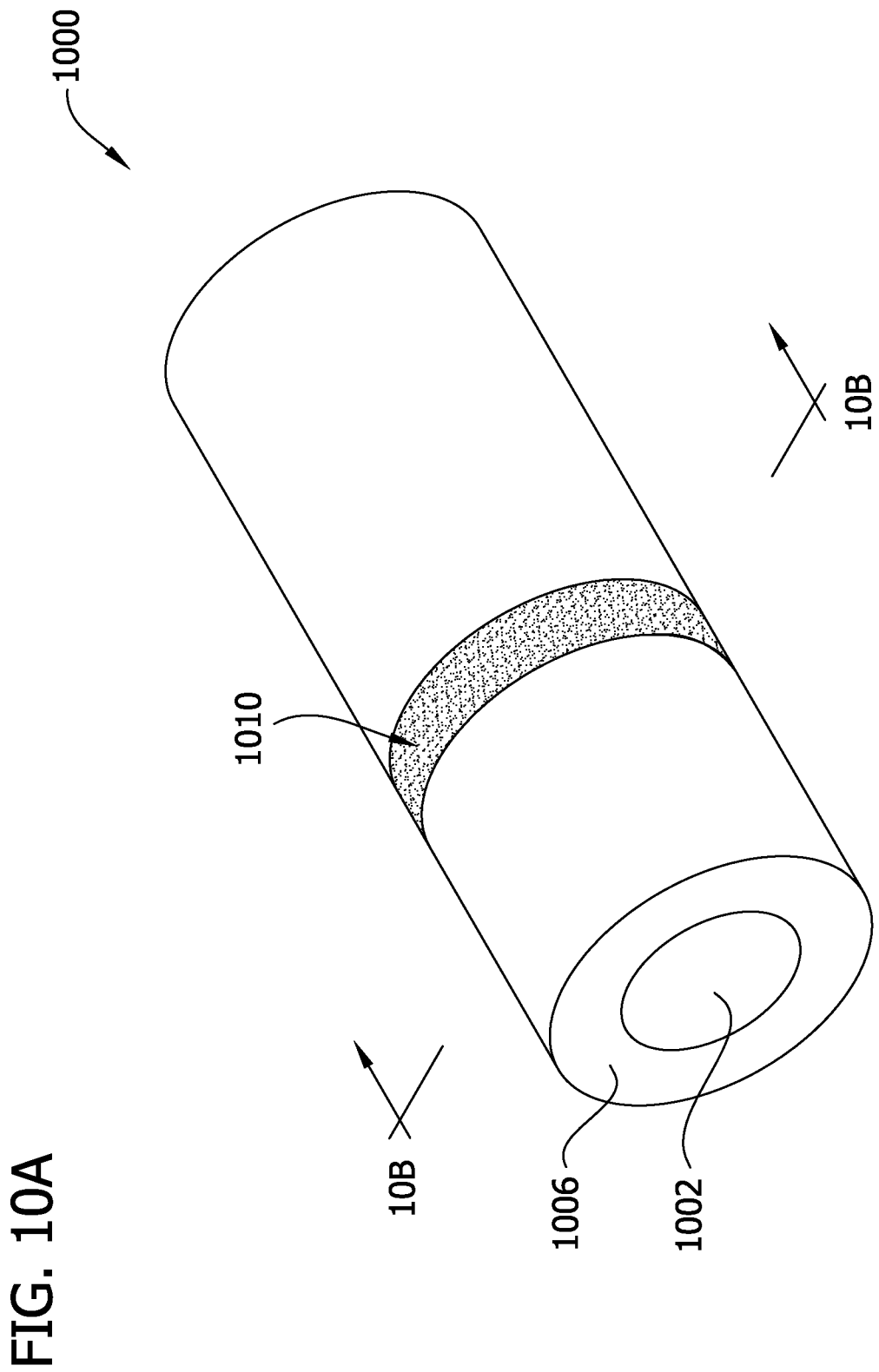

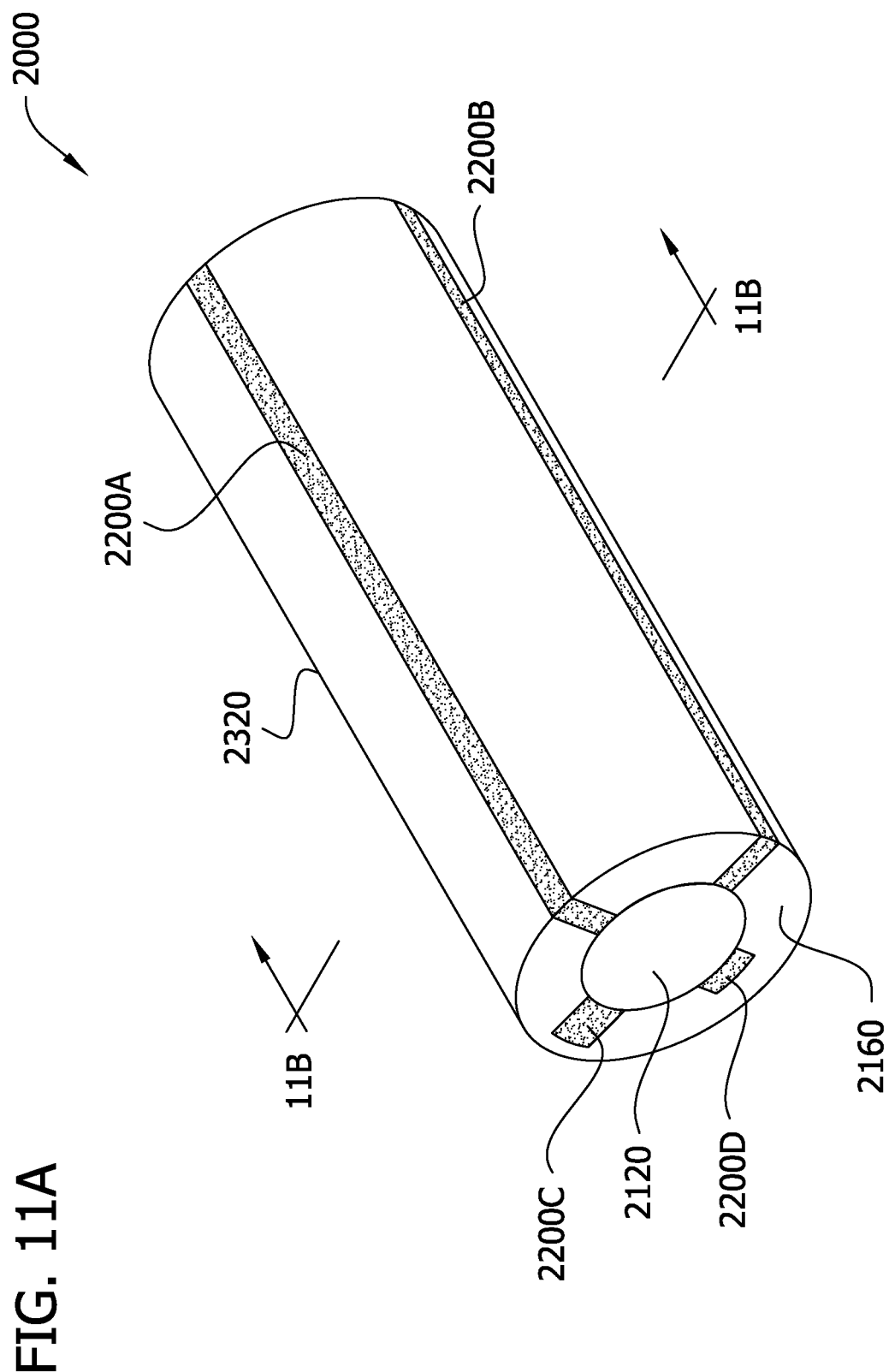

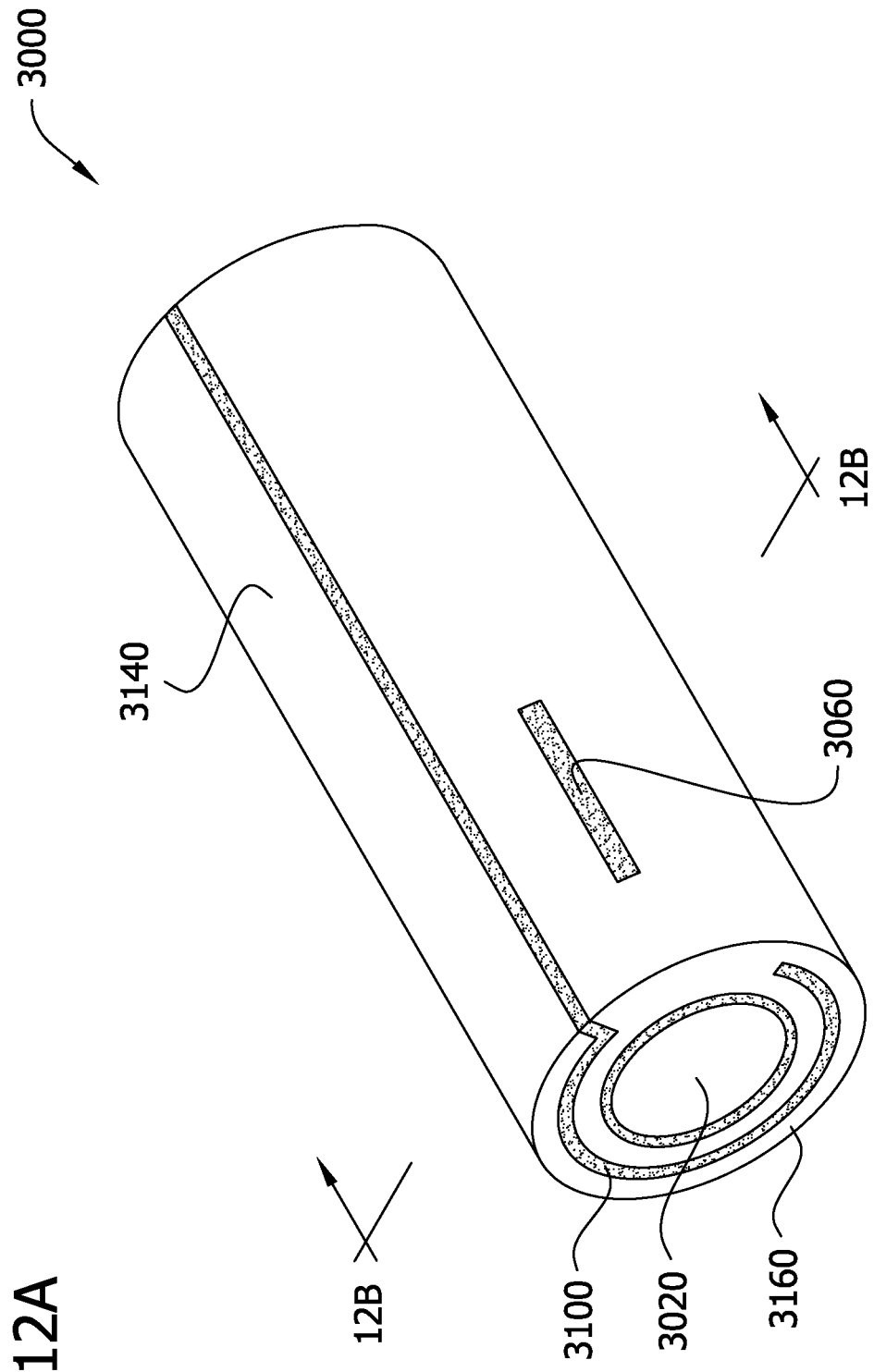

ELECTRICALLY CONDUCTIVE AND MECHANICALLY SUPPORTIVE POLYMER MATERIALS FOR BIOMEDICAL LEADS

REFERENCE TO RELATED APPLICATIONS

This application is a divisional application of U.S. patent application Ser. No. 13/044,492, filed Mar. 9, 2011, which is a non-provisional application of U.S. Provisional Patent Application Ser. No. 61/312,241, filed Mar. 9, 2010. The entire contents of the above applications are hereby incorporated by reference.

FIELD OF THE INVENTION

The present invention generally relates to materials and methods of fabricating biomedical leads. In particular, this invention is based upon using conductive and mechanically supportive materials in the wires/cables/leads of biomedical devices that interact with cardiac, neural, cochlear, and other tissues of the body for sensing and delivering electrical signals.

BACKGROUND OF THE INVENTION

Biomedical leads (including electrodes) are a primary component of many implantable medical devices including cardiac pacemakers and defibrillators, deep brain stimulation devices, cochlear implants, peripheral nerve (sacral, phrenic, vagal, etc.) stimulation devices, and spinal cord stimulation devices for pain management. The lead is used to transmit electrical signals to and from a device interface (e.g. a pulse generator) and one or more electrodes located near the tip or within the body of the lead (as shown in FIG. 1) and which is implanted into the appropriate target tissue (brain, nerve, muscle, heart, etc.), and a device interface.

Many implantable biomedical devices require quick, efficient, and accurate signal transduction through the lead in order to appropriately monitor and record bio-electrical activity, and to deliver therapeutic electrical signals. For example, cardiac pacemakers and cardiac resynchronization therapy electrically monitor the heart's activity and then deliver electrical pulses to regulate cardiac contractions. Deep brain stimulators are used to monitor neural activity and deliver therapeutic pulses to prevent the dyskinesia associated with Parkinson's disease, or to detect and/or prevent the onset of a seizure. Spinal cord stimulation involves the delivery of electrical pulses to electrodes implanted in or near the spinal cord in order to counteract chronic pain. Cochlear implants provide auditory sensation to persons with severe hearing loss by sending acoustic information in the form of electrical signals to an array of small metal electrodes implanted within the cochlear structure in the inner ear. Electrical signals sent to the vagus nerve, sacral nerve, and other targets in the peripheral nervous system are used to treat a number of diseases and disorders such as obesity, chronic pain, urinary incontinence, loss of diaphragm control, heart failure, and hypertension. Implantable cardio-defibrillators monitor cardiac activity and upon observing heart failure deliver large electrical shocks to restore cardiac function.

A major concern with such conventional leads is fracture. The consequences of lead fracture can be quite severe. In the case of implantable cardioverter defibrillators (ICDs), lead fracture produces inaccurate sensing of cardiac activity which can result in either inappropriate shock of the patient—a painful and traumatic experience that can damage the heart or surrounding tissue—or worse, the device can fail to shock when needed, possibly leading to death of the patient.

SUMMARY OF THE INVENTION

The medical leads of the invention avoid the problems and inconveniences associated with conventional leads. According to aspects of the invention, an implantable medical lead comprises a conducting electrode with a proximal end for receiving or delivering electrical signals, as well as a distal end. The lead also comprises a conductor having a body, a proximal end connected to the distal end of the conducting electrode to form a first electrical connection, and a distal end for connection to a device header to form a second electrical connection. The lead also comprises a conductive polymer in electrical contact with at least a portion of the medical lead. The lead additionally comprises an insulating sheath surrounding the conductive polymer to electrically insulate a surface of the conductive polymer.

The portion of the medical lead comprises a portion of the conductor. The conductive polymer may be part of a thermosetting polymer in contact with the portion of the lead or the portion of the conductor. The thermosetting polymer is a polymer comprising one or more of the following: polyurethane, silicone, epoxy, PEEK (poly ether ether ketone), acrylic, cyanoacrylate, epoxides, polyester, and vinyl ester.

The conductive polymer may be part of a conductive coating having a thickness ranging from 0.5 μm to 1,000 μm, from 5 μm to 500 μm, or from 20 μm to 100 μm. The conductive coating may be part of a heat shrinkable wrap.

The conductive polymer may be part of a conducting sleeve, where the conductor is placed in a lumen of said conducting sleeve. The conducting sleeve may have a wall thickness ranging from 0.5 μm to 1,000 μm, from 5 μm to 500 μm, or from 20 μm to 100 μm.

The implantable medical lead may further comprise an insulating sleeve, where the conductive polymer is coated or deposited onto an inner surface of the insulating sleeve, and where the conductor is placed in a lumen of the insulating sleeve, the insulating sleeve having a wall thickness. The wall thickness ranges from 0.5 μm to 1,000 μm, from 5 μm to 500 μm, or from 20 μm to 100 μm. The conductive polymer penetrates the insulating sleeve to a depth that is equal to or less than the wall thickness of the insulating sleeve. The conductive polymer may penetrate a length equal to or less than a total length of the insulating sleeve. The conductive polymer may penetrate a surface area equal to or less than a total surface area of the insulating sleeve. Distribution of the conductive polymer on the insulating sleeve may be non-uniform.

The conductive polymer may be in electrical contact with the first electrical connection and the conductor, and/or the conducting electrode, and/or the second electrical connection. Additionally or in alternative, the conductive polymer may be in electrical contact with the conductor, the second electrical connection and the device header.

Aspects of the invention are also directed to an implantable medical lead comprising a conducting electrode with a proximal end for receiving or delivering electrical signals, as well as a distal end. The lead also comprises a conductive polymer having a body, a proximal end connected to the distal end of the conducting electrode to form a first electrical connection, and a distal end for connection to a device header to form a second electrical connection. The lead additionally comprises an insulating sheath surrounding the conductive polymer to electrically insulate a surface of the conductive polymer.

The implantable medical lead may further comprise a plurality of the conducting electrodes, a plurality of the conductive polymers, where each conductive polymer corresponding to one electrode of the plurality of conducting electrodes, and a plurality of the insulating sheaths for electrically insulating at least one of the plurality of conductive polymers. The plurality of conductive polymers may be arranged coaxially, in parallel, or a combination thereof.

The conductive polymer may comprise one or more of the following conducting materials: polypyrrole, polythiophene, polyethylenedioxythiophene (PEDOT), polyaniline, polyacetylene, natural or synthetic melanins, or a derivative, copolymer or homopolymer thereof. The conductive polymer may further comprise a dopant. The conductive polymer may be a reaction product of a polymerization mixture comprising about 30-100% (w/w) of conducting monomer, and 0-70% (w/w) of the dopant based on the total weight of the conducting monomer and the dopant in the polymerization mixture. Alternatively, the conductive polymer is a reaction product of a polymerization mixture comprising about 60-80% (w/w) of conducting monomer, and 20-40% (w/w) of the dopant based on the total weight of the conducting monomer and the dopant in the polymerization mixture. Alternatively, the conductive polymer is a reaction product of a polymerization mixture comprising about 90-100% (w/w) of conducting monomer, and 0-10% (w/w) of the dopant based on the total weight of the conducting monomer and the dopant in the polymerization mixture.

The dopant may comprise one or more of the following electrical dopants to impart conductivity: metal particles, metal nanoparticles, electroplated metals, carbon nanotubes, carbon fibers, graphite, an anionic molecule, a salt, a non-polymeric conductive macromolecule, or a polymeric anion. The dopant additionally or alternatively may also comprise one or more of the following mechanical dopants to improve mechanical strength of the conductive polymer: polystyrene sulfonate (PSS), polyacrylamide, polyacrylate, carbon fibers, carbon nanotubes, a copolymer with anionic segments, or a crosslinking agent. The dopant additionally or alternatively may also comprise one or more of the following deposition facilitator dopants to improve processability of the conductive polymer: a counterion, a surfactant, a photo-initiator, an oxidizing agent, a polymeric anion, or a copolymer with anionic segments. In general, the conductive polymer may comprise one or more electrical dopants, mechanical dopants, or processability dopants.

The insulating sheath described earlier may be a film, foam, sheet, mesh, or fabric made of one or more of the following insulating materials: silicone, polyurethane, polyimide, ethylene tetrafluoroethylene, polytetrafluoroethylene, poly ether ether ketone, or polyolefin. The electrical connections of the implantable medical lead may be soldered, welded, pressure fitted, or crimped connections.

The conductive polymer and/or the insulating sheath may be modified by exposure to oxidizing chemicals, acids, or a combination thereof to impart one or more of the following properties: wettability, permeability, porosity, adhesion, or texture. In addition or in alternative, the conductive polymer and/or the insulating sheath may be modified by exposure to a silane, a self-assembled monolayer, or a combination thereof to impart one or more of the following surface properties: wettability, permeability, porosity, adhesion, or texture.

The conductive polymer may penetrate the insulating sheath to a depth that is equal to or less than the wall thickness of the insulating sheath. In addition or in alternative, the conductive polymer may penetrate a length of the insulating sheath equal to or less than a total length of the insulating sheath. In addition or in alternative, the conductive polymer may penetrate a surface area of the insulating sheath equal to or less than a total surface area of the insulating sheath.

Monomeric units of the conductive polymer may polymerized onto a surface of the insulating sleeve by chemically-initiated polymerization, electrochemically-initiated polymerization, or photo-induced polymerization.

Other objects and features will be in part apparent and in part pointed out hereinafter.

BRIEF DESCRIPTION OF THE DRAWINGS

FIG. 2A is a perspective view of an implantable medical lead of this invention, including a conductive layer and an insulating sheath;

FIG. 2B is perspective view of the implantable medical lead of FIG. 2A with portions cut away to show details;

FIG. 3B is a perspective view of the implantable medical lead of FIG. 3A with portions cut away to show details;

FIG. 3F is a side view of the implantable medical lead of FIG. 3D with portions cut away to show details;

FIG. 6A is a perspective view of a conductive polymer conductor according to other aspects of this invention;

FIG. 6C is a side view of the conductive polymer conductor of FIG. 6A in use in an implantable medical lead and with portions cut away to show details;

FIG. 7A is a perspective view of a conductive polymer conductor according to other aspects of this invention;

FIG. 8B is a section taken in plane 8B-8B of FIG. 8A;

FIG. 10A is a perspective view of a conductor according to aspects of this invention having a polymer deposit formed thereon;

FIG. 11A is a perspective view of a conductor according to aspects of this invention having multiple, variable polymer deposits formed thereon;

FIG. 12A is a perspective view of a conductor according to other aspects of this invention having multiple, variable polymer deposits formed thereon;

Corresponding reference characters indicate corresponding parts throughout the drawings.

DESCRIPTION OF THE PREFERRED EMBODIMENTS

Figure 1:
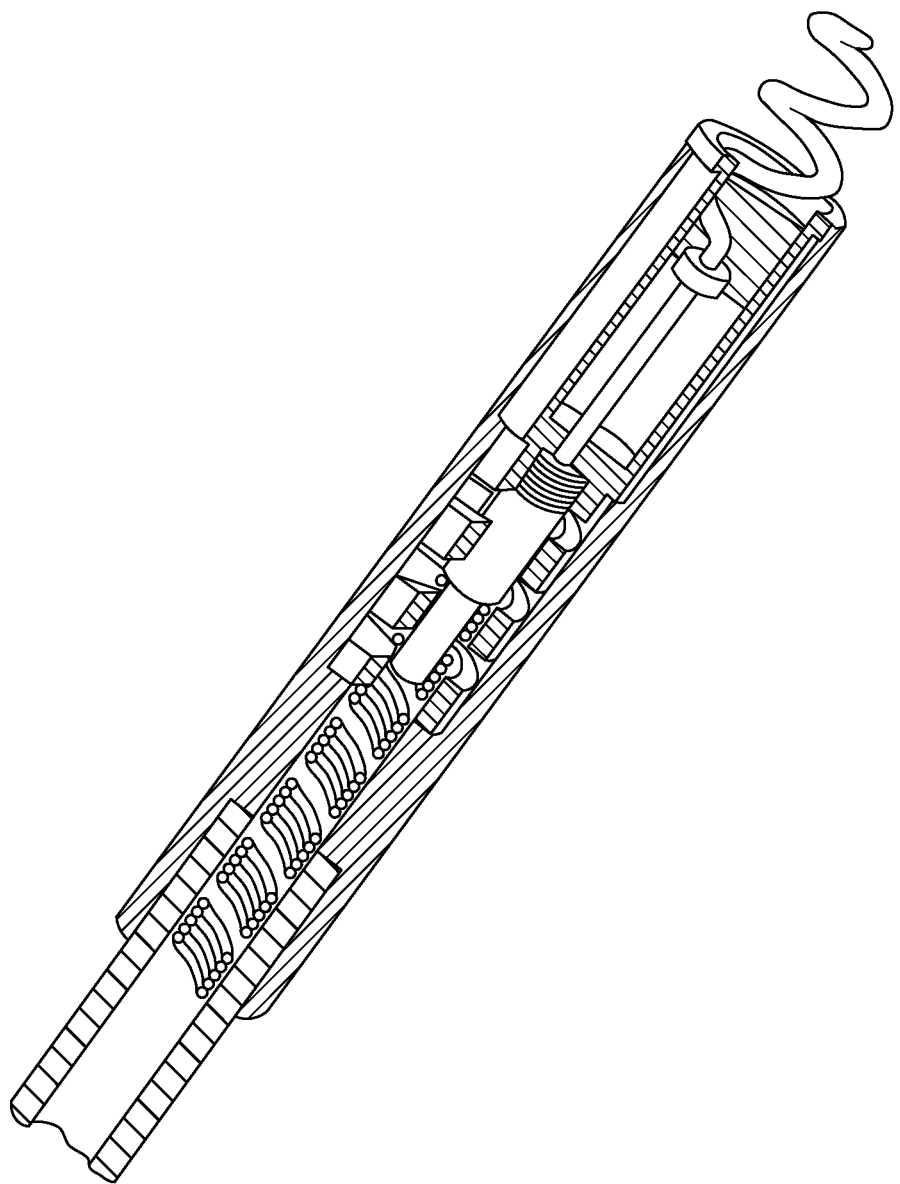
FIG. 1 is a schematic view of a conventional medical lead of the prior art.

Embodiments of the invention incorporate a conductive polymer composition into lead conductors to create soft, flexible conductors that are resistant to fracture or cracking. The ability to bridge physical and electrical gaps in a lead conductor with a structure made of the conductive polymer composition, and faithfully transmit electro-physiologically-relevant signals, was unexpected. If a metal conductor of the lead fractures during usage, the conductive polymer structure can keep the two segments of the fractured lead mechanically connected and in close proximity to each other, provide conductive pathways for the sensing signals or electrical stimulation pulses to circumvent the fractured section of conductor, and absorb some of the stress on the joints.

In other embodiments, the conductivity of a lead conductor is entirely by virtue of the conductive polymer composition. The structure of the conductive polymer composition on the lead is both mechanically compliant so that it can flex with movement of the lead, and electrically conductive with low impedance characteristics, and ideally does not contribute to the overall lead impedance.

Referring to FIGS. 2A-D, an implantable medical lead according to this invention is generally designated by the reference 20. In general, lead 20 comprises a conducting electrode 22, a conductor 26, a conductive polymer layer 50, an insulating sheath 54 formed on the polymer layer, and a device header 30 in an arrangement as illustrated.

Figure 2C:
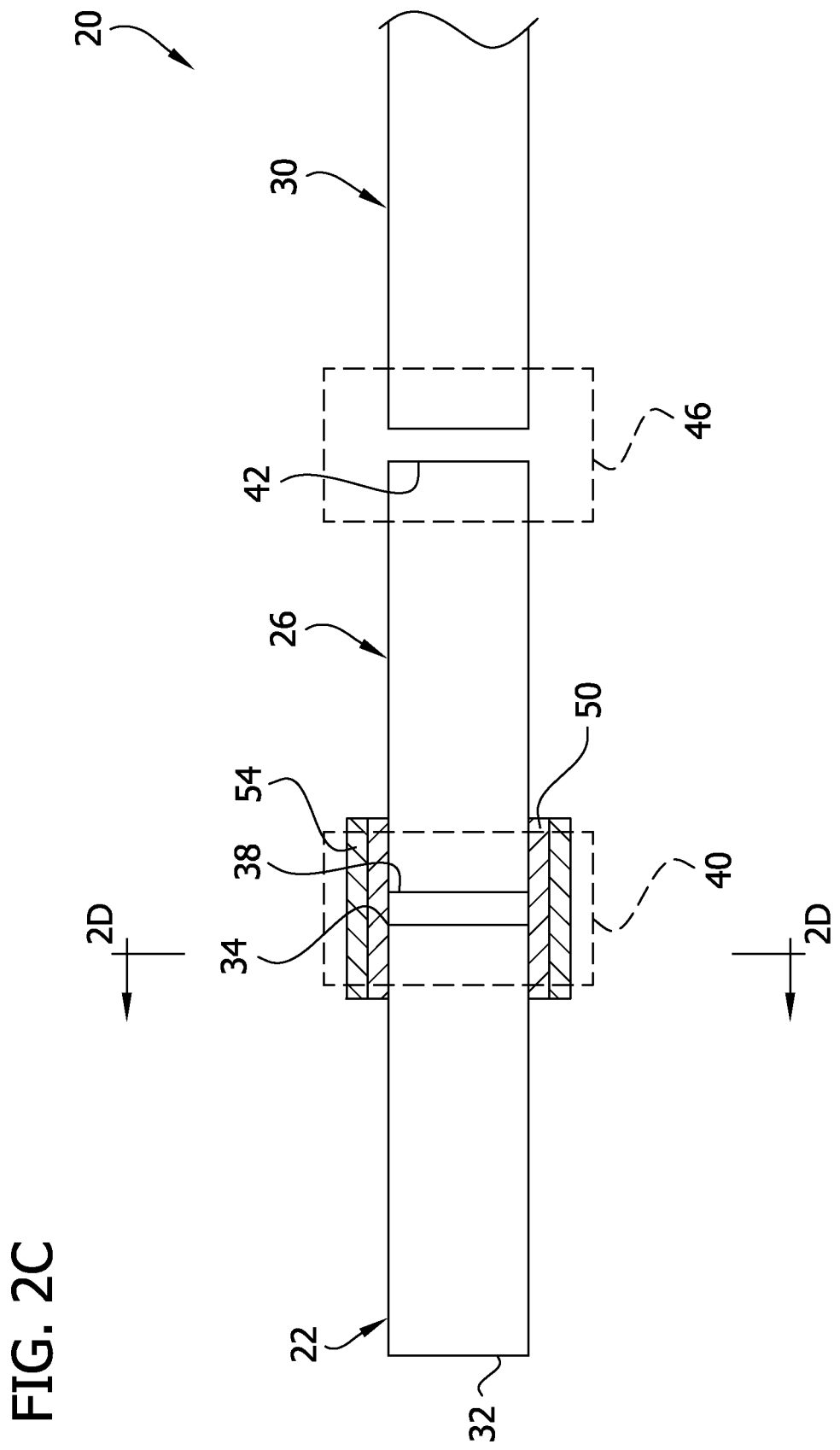
FIG. 2C is a side view of the implantable medical lead of FIG. 2A with portions cut away to show details.
Figure 2D:
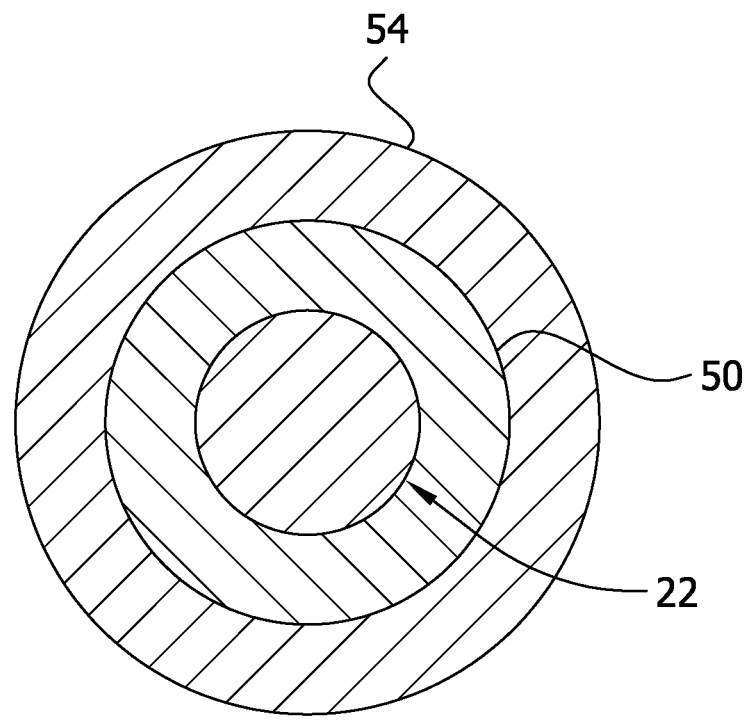
FIG. 2D is a section taken in the plane 2D-2D of FIG. 2C.

As best shown in FIG. 2C, electrode 22 has a proximal end 32 that interfaces with body tissue for either delivering or receiving electrical signals. A distal end 34 of electrode 22 interfaces with a proximal end 38 of the conductor 26 to form a first electrical connection 40 that provides electrical continuity. First electrical connection 40 may be formed in any way as is known in the art, such as but not limited to welding, soldering, pressure fitting, or crimping. In some embodiments (not shown), first electrical connection 40 may include an additional biosensor, an analysis unit, or other component. Similarly, a distal end 42 of the conductor 26 interfaces the device header component 30 (e.g. a wire of a medical device) to form a second electrical connection 46.

While illustrated in a component format for simplicity of presentation, variations in design (diameter, shape of each individual component, positioning of the components with respect to each other, etc.) of the electrode 22, conductor 26, and header 30 are within the scope of the invention. For example, the invention may substantially conform to the medical lead of FIG. 1 with the inclusion of a conductive polymer layer and an insulating sheath as disclosed herein.

FIGS. 2A-D illustrate formation of the conductive polymer layer 50 and the insulating sheath 54 on the electrode side of the first connection 40. A conductive polymer composition is deposited as the polymer layer 50 to cover or surround the first electrical connection 40, thereby connecting the electrode 22 and the conductor 26. Desirably, the use of polymer layer 50 and insulating sheath 54 provides conductive and mechanical support to the lead 20 to prevent failure in the event that the first electrical connection 40 fractures or otherwise fails. In other words, conductive polymer layer 50 provides conductive pathways for the electrical signals to bypass any fractured sections. Polymer layer 50 and insulating sheath 54 together also serve to keep disconnected segments of a fractured lead in close proximity to each other.

Figure 3A:
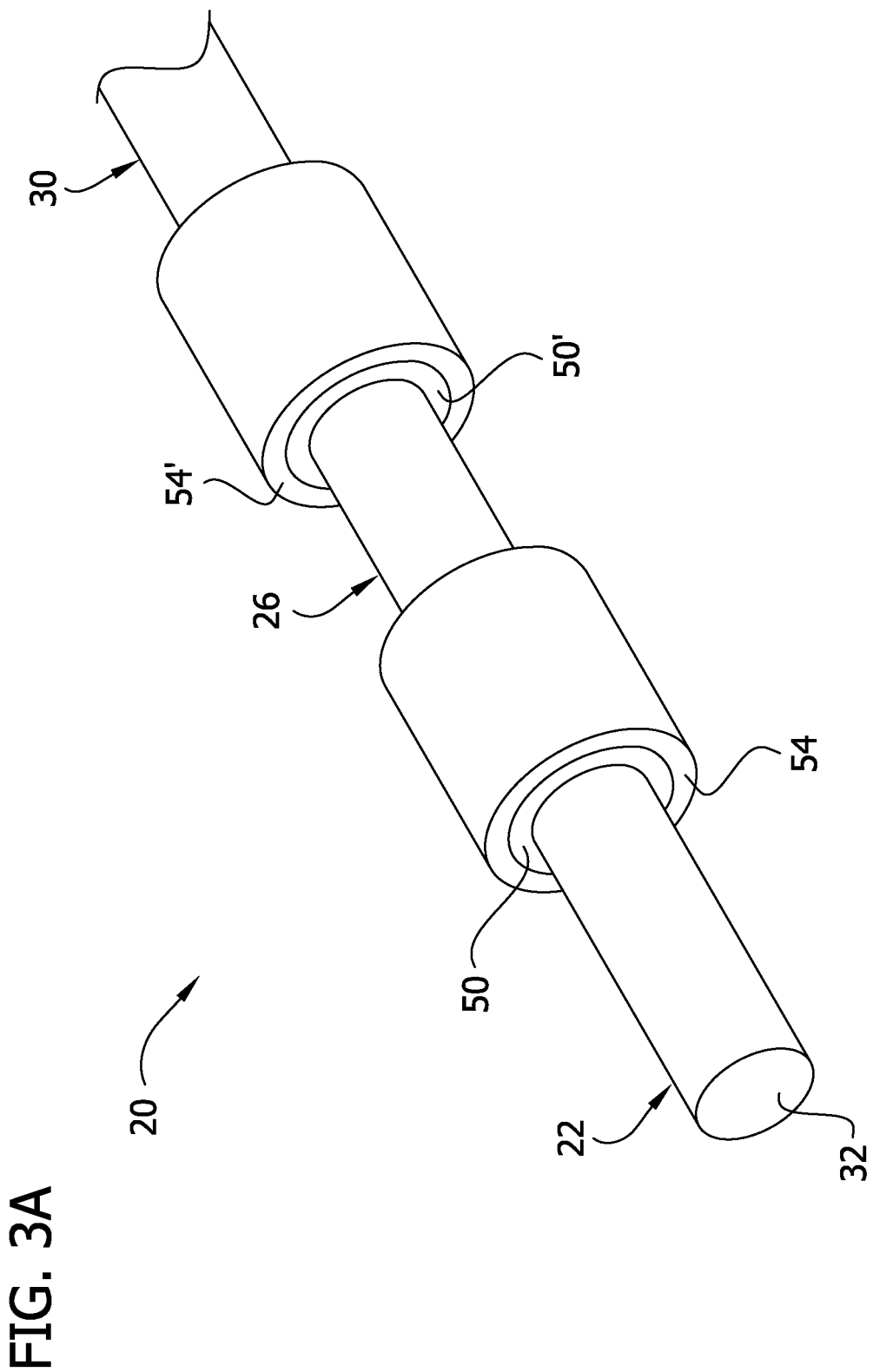
FIG. 3A is a perspective view of the implantable medical lead of FIG. 2A having an additional conductive layer and an additional insulating sheath.
Figure 3C:
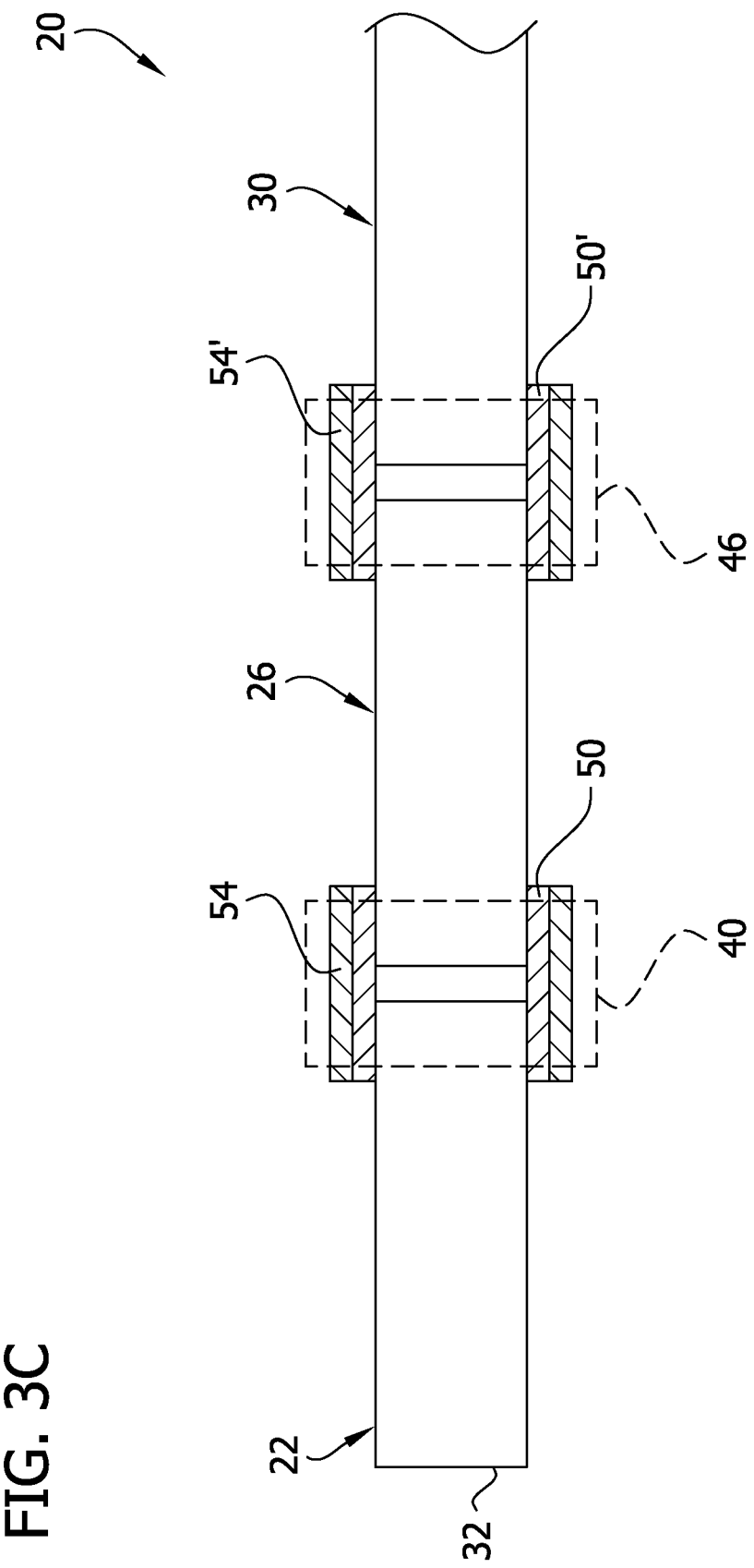
FIG. 3C is a side view of the implantable medical lead of FIG. 3A with portions cut away to show details.
Figure 3D:
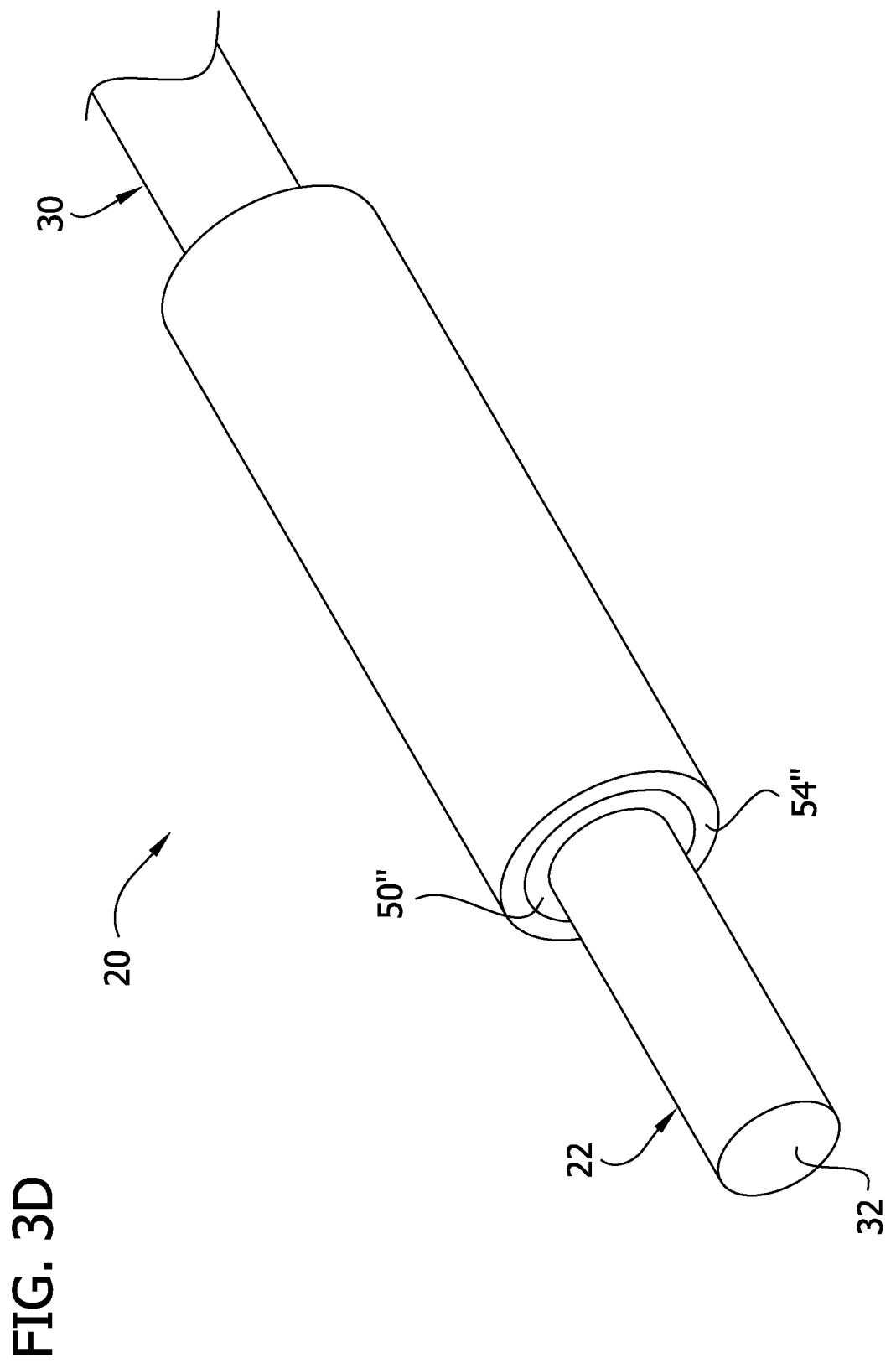
FIG. 3D is a perspective view of the implantable medical lead of FIG. 2A having a conductive layer and an insulating sheath extending between the first connection and the second connection.
Figure 3E:
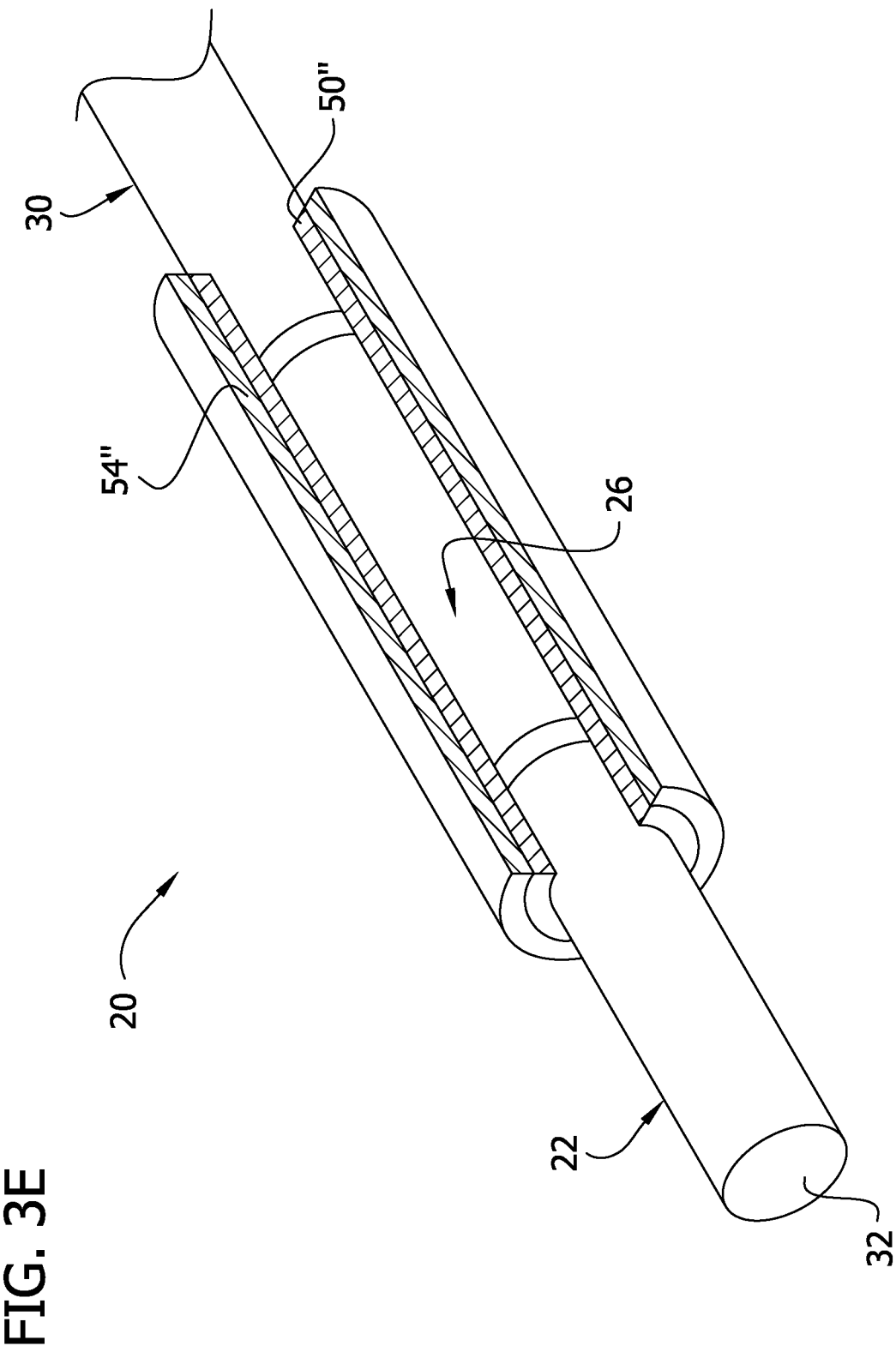
FIG. 3E is a perspective view of the implantable medical lead of FIG. 3D with portions cut away to show details.
Figure 4A:
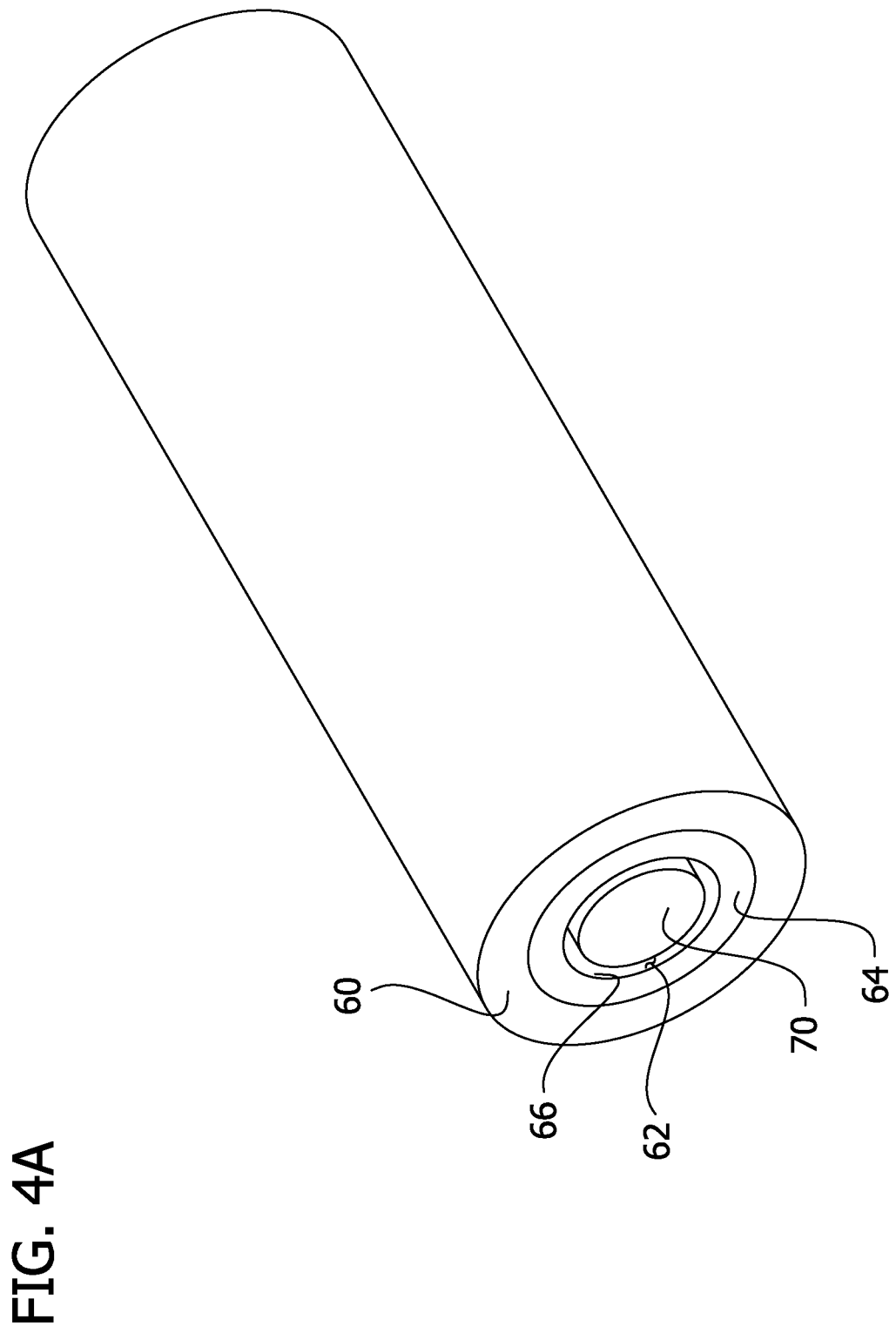
FIG. 4A is a perspective view of a lead component according to aspects of this invention having conductive polymer composition deposited on the insulating sleeve.
Figure 4B:
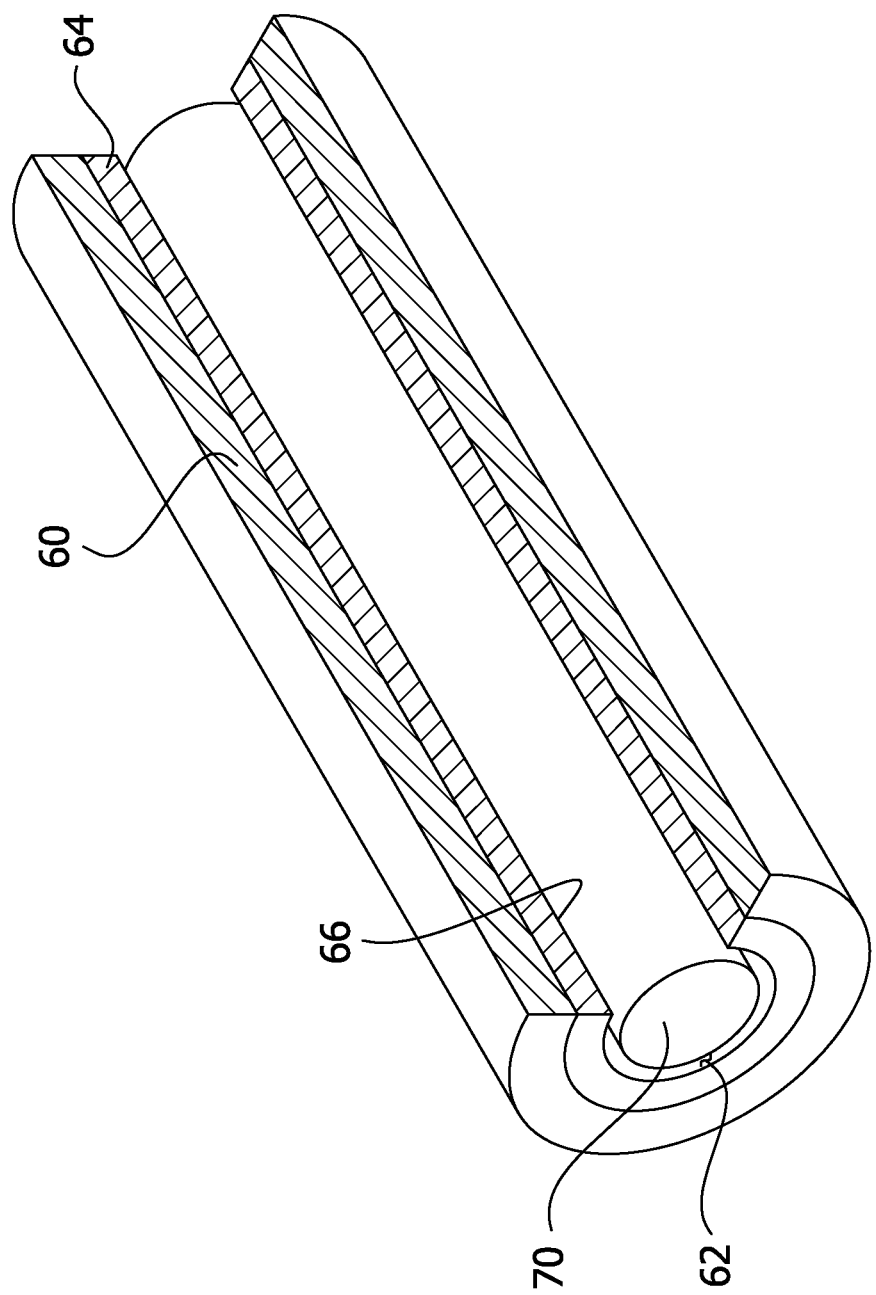
FIG. 4B is a perspective view of the lead component of FIG. 4A with portions cut away to show details.
Figure 4C:
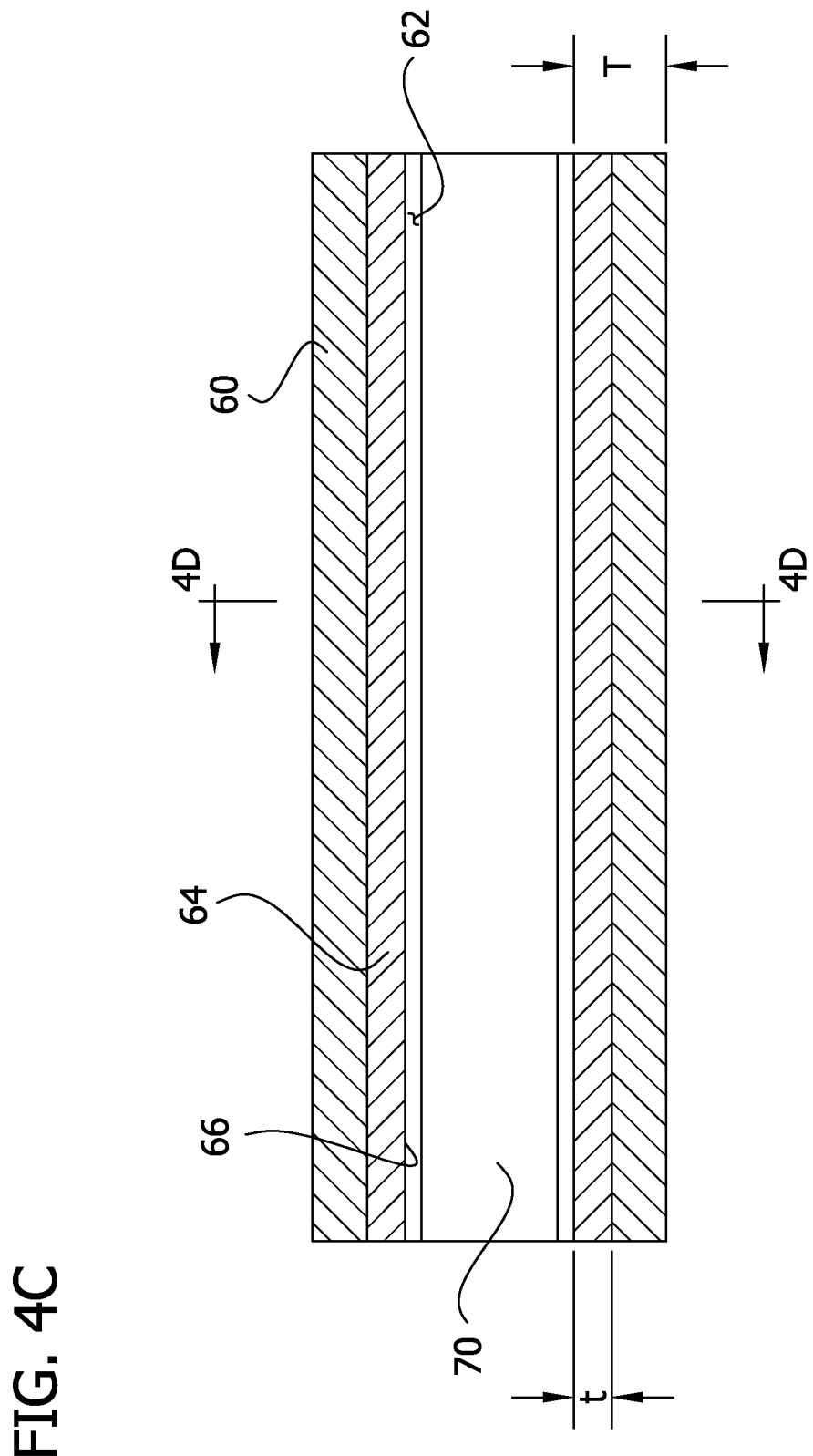
FIG. 4C is a side view of the lead component of FIG. 4A with portions cut away to show details.
Figure 4D:
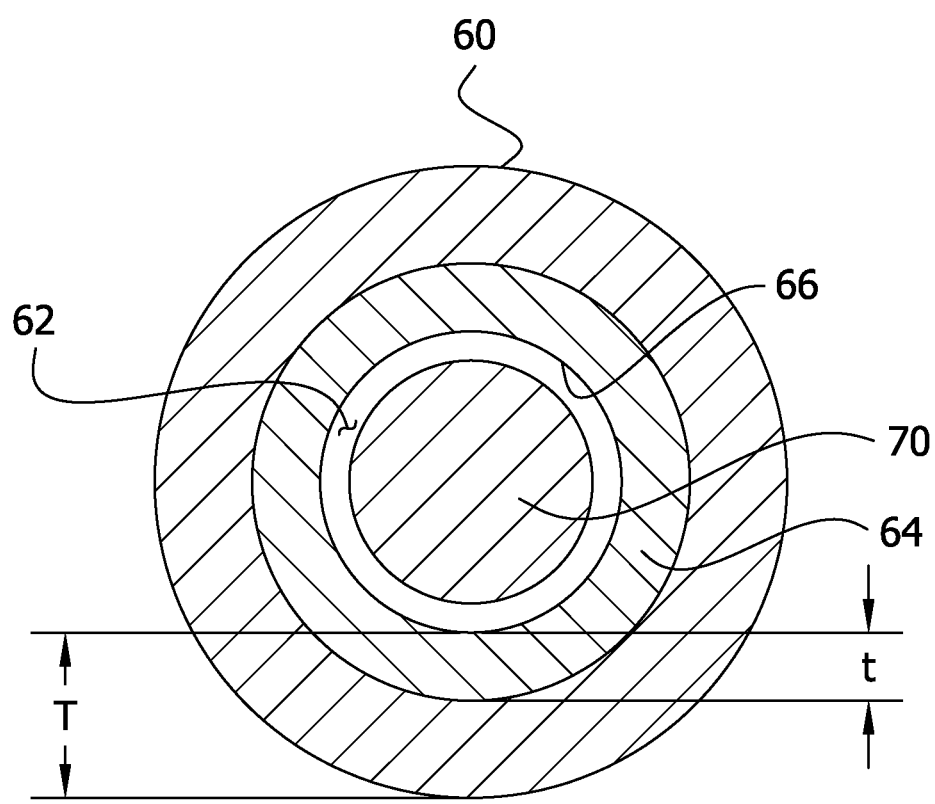
FIG. 4D is a section taken in the plane 4D-4D of FIG. 4C.

In a manner similar to FIGS. 2A-D, the polymer may alternatively (not shown) or in addition (see FIGS. 3A-C) be formed around the second electrical connection 46 as a second conductive polymer layer 50', along with a second insulating sheath 54'. FIGS. 3D-F illustrate an embodiment where polymer layer 50" (and sheath 54") covers the first connection 40, the entire length of the conductor 26, and the second connection 46. Fracture at connections (such as first connection 40 and/or second connection 46) within leads is frequently observed, and this invention is operable for placement of the polymer 50" and sheath 54" in a continuous or discontinuous manner at one or more positions along the lead 20 (e.g. the embodiments of FIGS. 2 and 3A), as deemed necessary by the electrical and mechanical demands placed on the lead by the particular medical application.

Using FIGS. 2A-D for descriptive purposes (but extensible to any of the embodiments of the invention), conductive polymer layer 50 may be formed on the lead 20 by any suitable means. In one embodiment, polymer layer 50 is formed as a coating of the conductive polymer composition on the lead 20. In another embodiment, the conductive polymer composition is suspended or part of a thermosetting polymer such as an epoxy resin, and the polymer layer 50 is composed of a resin layer, coating, or deposit that incorporates the conductive polymer composition. In another embodiment, conductive layer 50 is a preformed, heat-shrinkable wrap formed of the conductive polymer or incorporating the conductive polymer, the fabrication of which is described in detail below. In yet another embodiment, the polymer layer 50 is formed as a sleeve or tube of the conductive polymer composition, and the lead 20 is placed in a lumen of the tube. A layer, coating or deposit that incorporates the conductive polymer composition includes any layer, coating or deposit including sufficient conductive polymer composition to maintain an electrical connection. For example, the conductive polymer composition can be dispersed in a thermosetting polymer such as an epoxy resin layer that is applied to the lead 20.

Continuing to describe conductive polymer layer formation on one or more lead component(s), in another embodiment as illustrated in FIGS. 4A-D, an insulating sheath 60, instead of a conductive polymer layer, is formed as a tubing having a lumen 62 in which the lead component 70 is placed. The reference number 70 may be used to refer to any component of the lead (first electrical connection, second electrical connection, conductor, etc.). The conductive polymer composition is deposited or coated onto an inner surface 66 of the sheath 60 as a conductive layer 64 prior to placement of the lead 70. Inner surface 66 is in contact with lead 70, with the space between these elements in FIG. 4A merely illustrating the existence of the lumen 62. Preferably the conductive polymer composition penetrates the sheath 60 to a depth t that is preferably (but not necessarily) less than the total thickness T of the sheath 60. When t is less than T, this approach advantageously preserves the insulating nature of the sheath 60 while increasing conductivity in the vicinity of the lead 70. Further, deposition of the conductive polymer composition on surface 66 may be uniform or non-uniform. Non-uniform, heterogeneous, patterned, or otherwise restricted deposition of the polymer composition is beneficial for creating connections or electrodes, as will be described using exemplary embodiments below. For example, selected areas where the conductive polymer extends all the way through the insulation can be used for connections between the lead 70 and the header or the electrode.

Figure 5A:
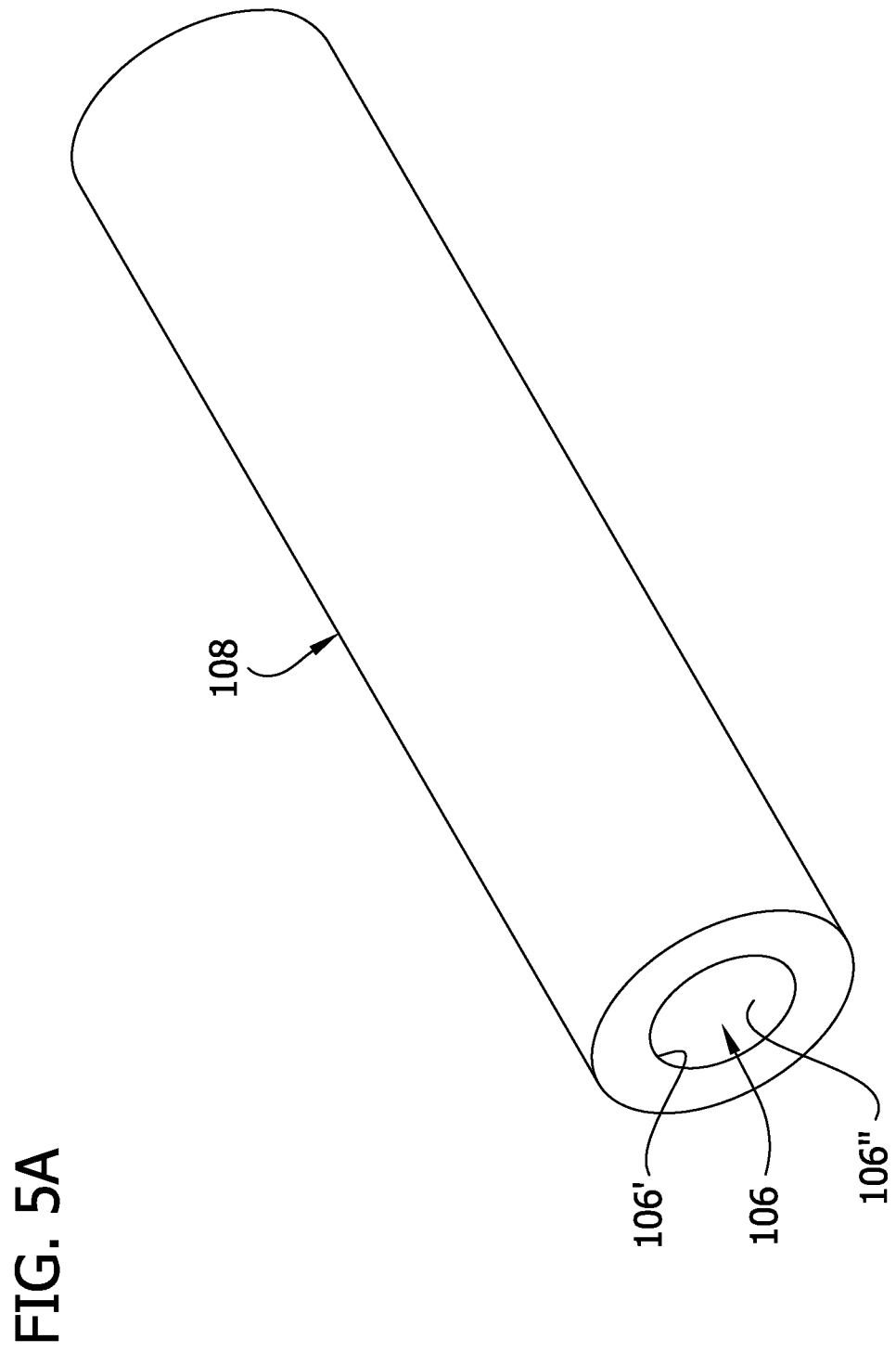
FIG. 5A is a perspective view of a conductive polymer conductor according to aspects of this invention having a conductive polymer core surrounded by an insulating sleeve.
Figure 5B:
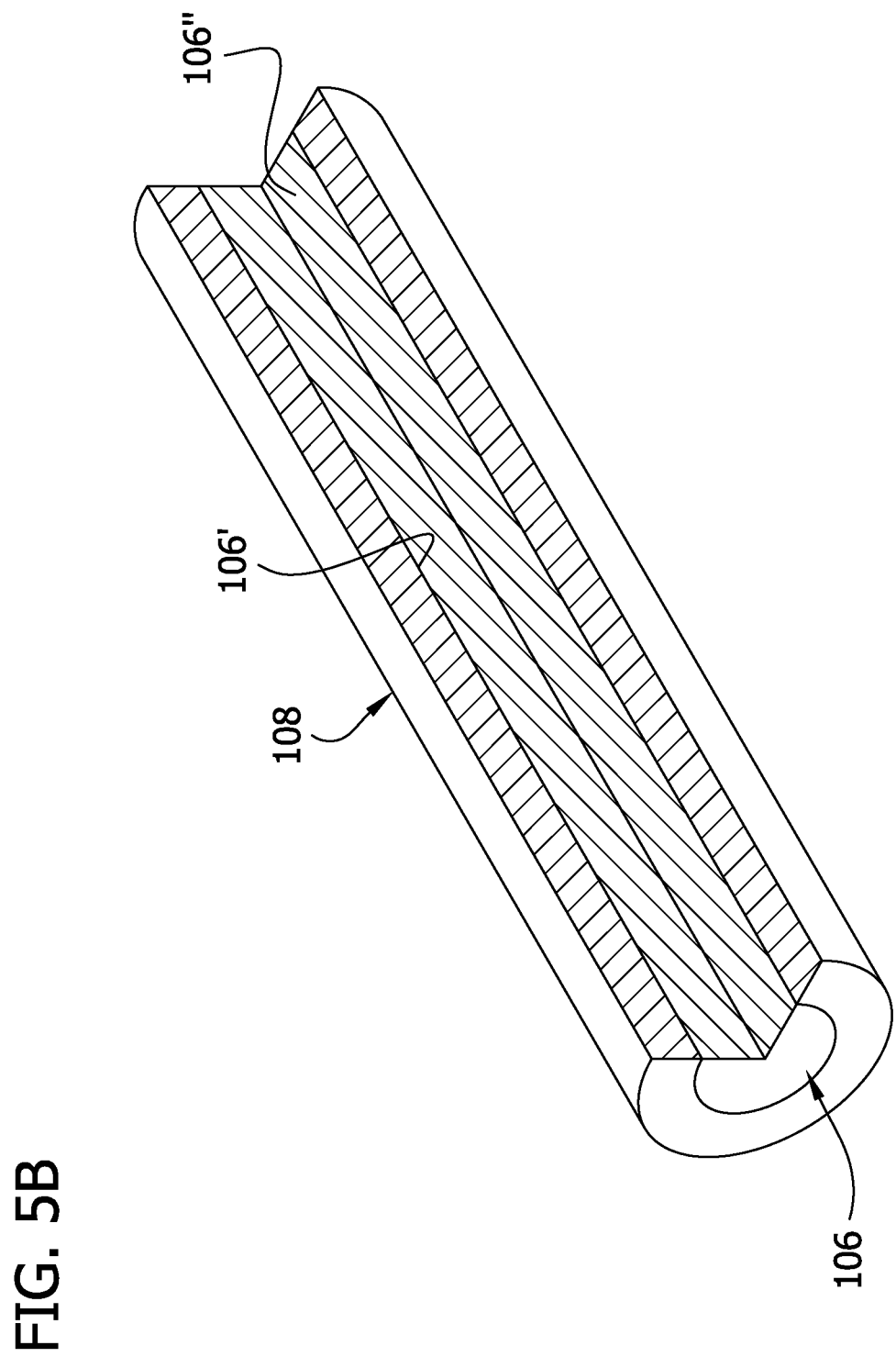
FIG. 5B is a perspective view of the conductive polymer conductor of FIG. 5A with portions cut away to show details.
Figure 5C:
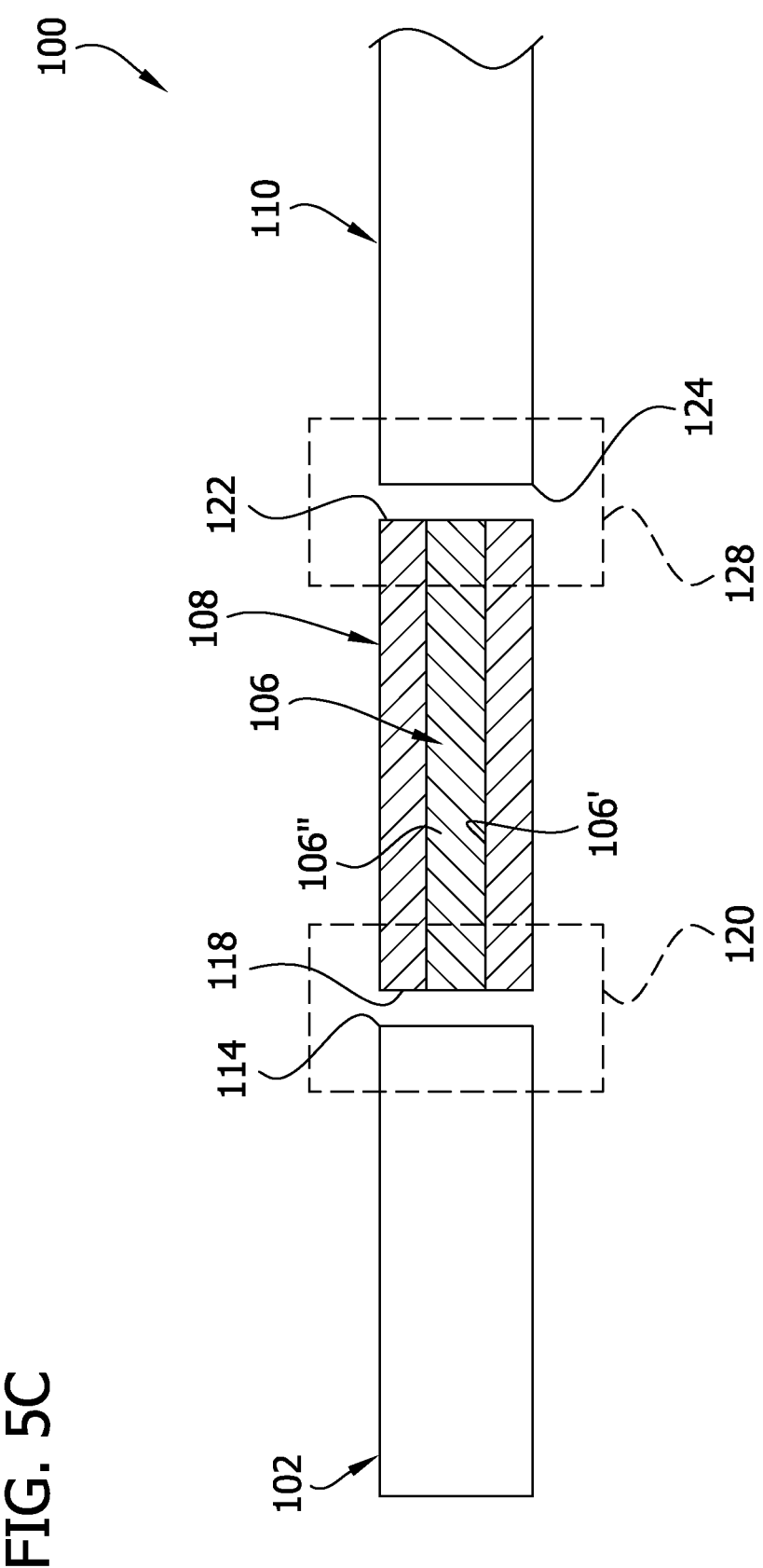
FIG. 5C is a side view of the conductive polymer conductor of FIG. 5A in use in an implantable medical lead and with portions cut away to show details.
Figure 6B:
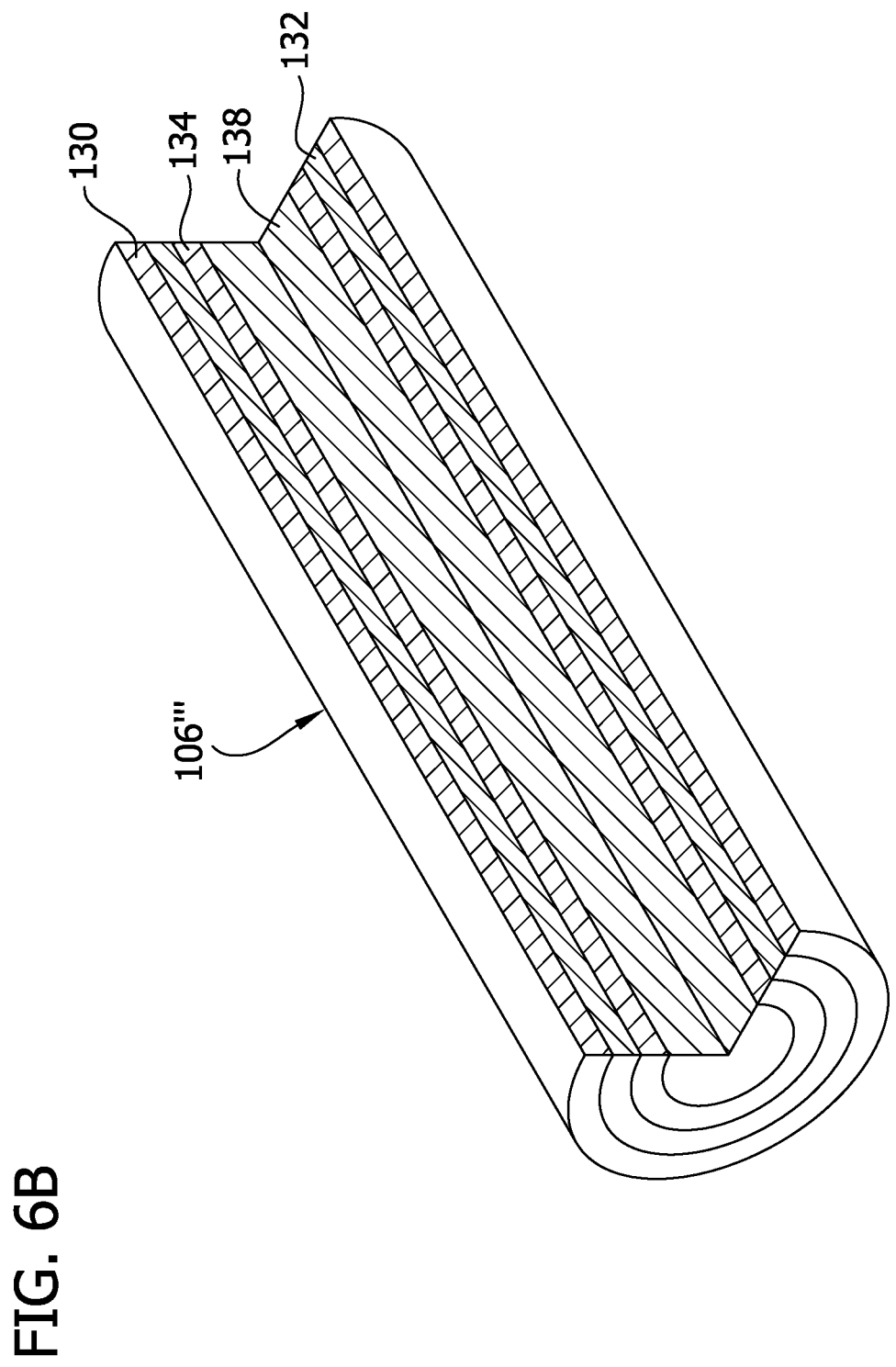
FIG. 6B is a perspective view of the conductive polymer conductor of FIG. 6A with portions cut away to show details.
Figure 6D:
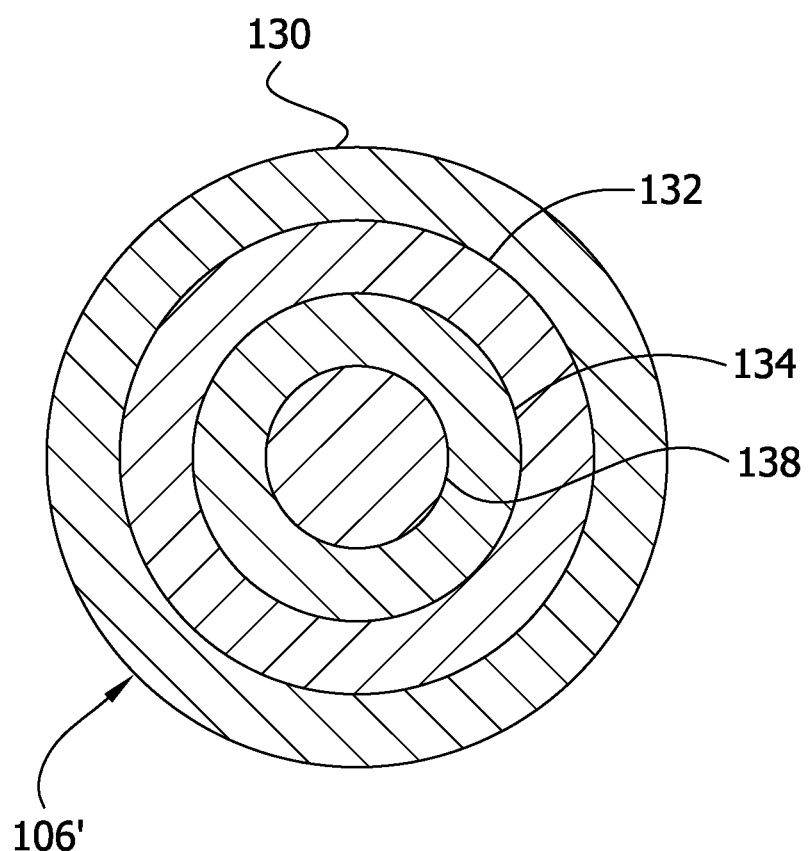
FIG. 6D is a section taken in the plane 6D-6D of FIG. 6C.

Referring to FIGS. 5A-C, an implantable medical lead according to another embodiment of this invention is generally designated by the reference 100. Lead 100 comprises a conducting electrode 102, a conductive polymer component 106, an insulating sheath 108 formed on the conductive polymer component, and a device header 110 in an arrangement as illustrated.

Significantly, in contrast to aforementioned embodiments where a polymer layer provides a secondary or a backup electrical path to a conventional conductor, a conductive polymer conductor such as polymer component 106 in FIGS. 5A-C entirely replaces conventional conductors in medical leads to provide the primary conductive means for lead operation. A distal end 118 of the polymer component 106 forms a first electrical connection 120 with a proximal end 114 of the conducting electrode 102, and a proximal end 122 of the polymer component forms a second electrical connection 128 with the distal end 124 of the device header 110 for electrical and mechanical continuity. Insulating sheath 108 surrounds and insulates a surface 106' of the polymer component 106. Sheath 108 may extend onto any of the first electrical connection 120, the second electrical connection 128, the electrode 102, and/or the device header 110. Polymer component 106 has a body 106" comprised of the conductive polymer composition as discussed above.

In alternative embodiments, the body 106" of the polymer component 106 is formed of a thermosetting polymer such as an epoxy resin, or an insulating member that is rendered conductive by having the conductive polymer composition suspended within body 106". In other or additional embodiments, the conductive polymer composition may be coated or deposited on the surface 106' of a non-conductive body 106, or provided as a heat shrinkable wrap around the non-conductive body 106 as described above.

Referring to FIGS. 6A-D, an implantable medical lead according to another embodiment of this invention is generally designated by the reference 100'. Lead 100' comprises one or more conducting electrodes 102', a conductor 106" comprising multiple conductive polymer conductors such as conductive polymer components 132, 138 for providing a plurality of parallel conductive paths, and also comprising multiple insulating sheaths 130, 134. It is possible, in other embodiments, for multiple conducting electrodes to interface all polymer components In the illustrated embodiment, each conductive polymer component 132, 138 is in contact with the electrode 102' to provide electrical continuity. For example, polymer component 132 may be used for delivering electrical signals to the electrode 102', while polymer component 138 is used for receiving electrical signals from the electrode, or vice versa. Each polymer component 132, 138 is in contact with at least one insulating sheath 130, 134 for electrical isolation from other conductive polymer components. Several configurations are possible. FIGS. 6A-D illustrate a coaxial arrangement of two conductive polymer layers 132, 138 separated by insulating sheaths 130, 134. Alternatively, reference elements 130, 134 can represent conductive polymer layers while elements 132, 138 correspond to insulating sheaths, in which case an additional insulating sheath (not shown) may be formed over outermost polymer layer 130. In such embodiments where multiple layers of conductive polymers are used, the composition of each layer may be identical or different. Similar, the composition of each insulating sheath may be identical or different.

Figure 7B:
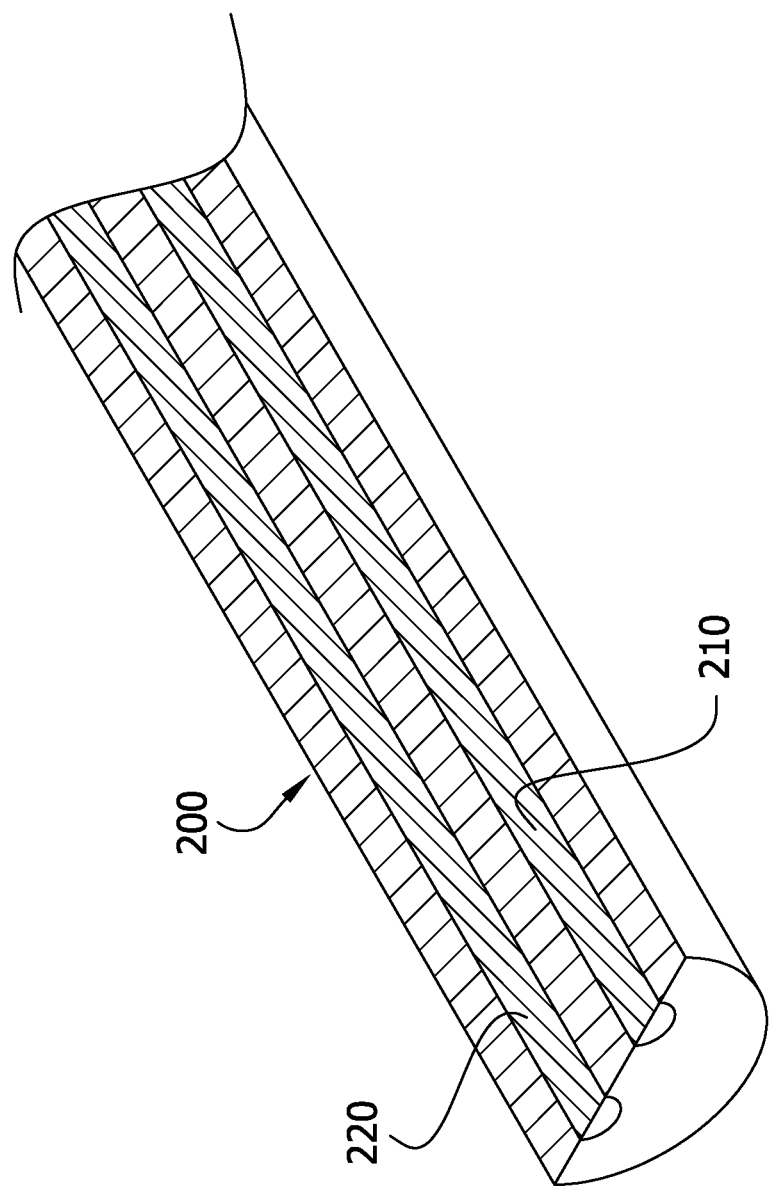
FIG. 7B is a section taken in plane 7B-7B of FIG. 7A.
Figure 7C:
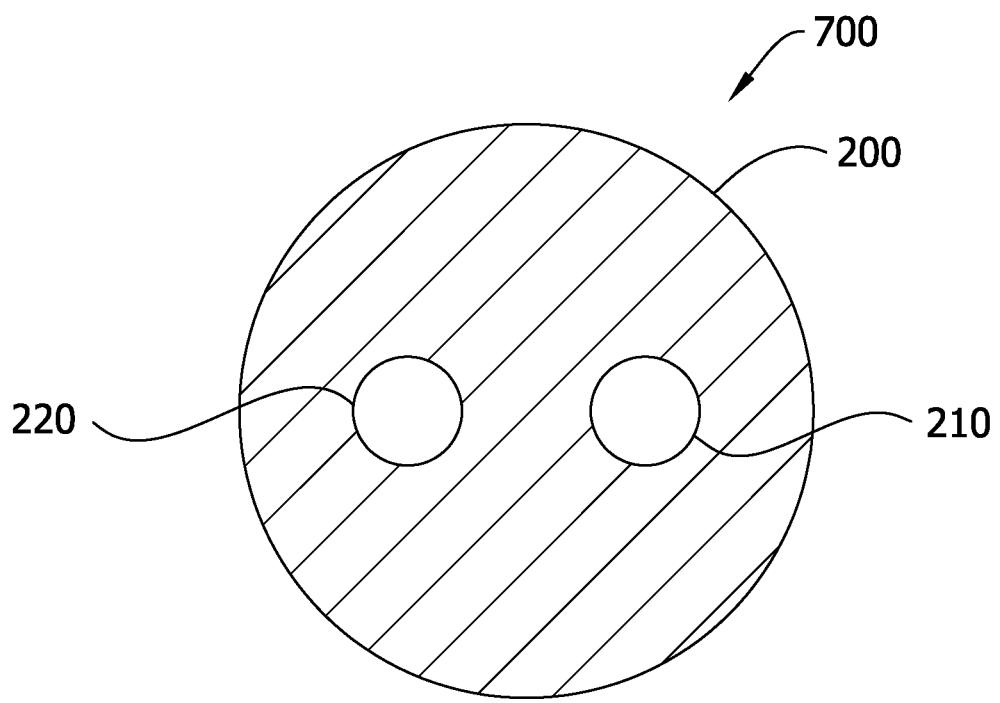
FIG. 7C is a section taken in plane 7C-7C of FIG. 7A.
Figure 8A:
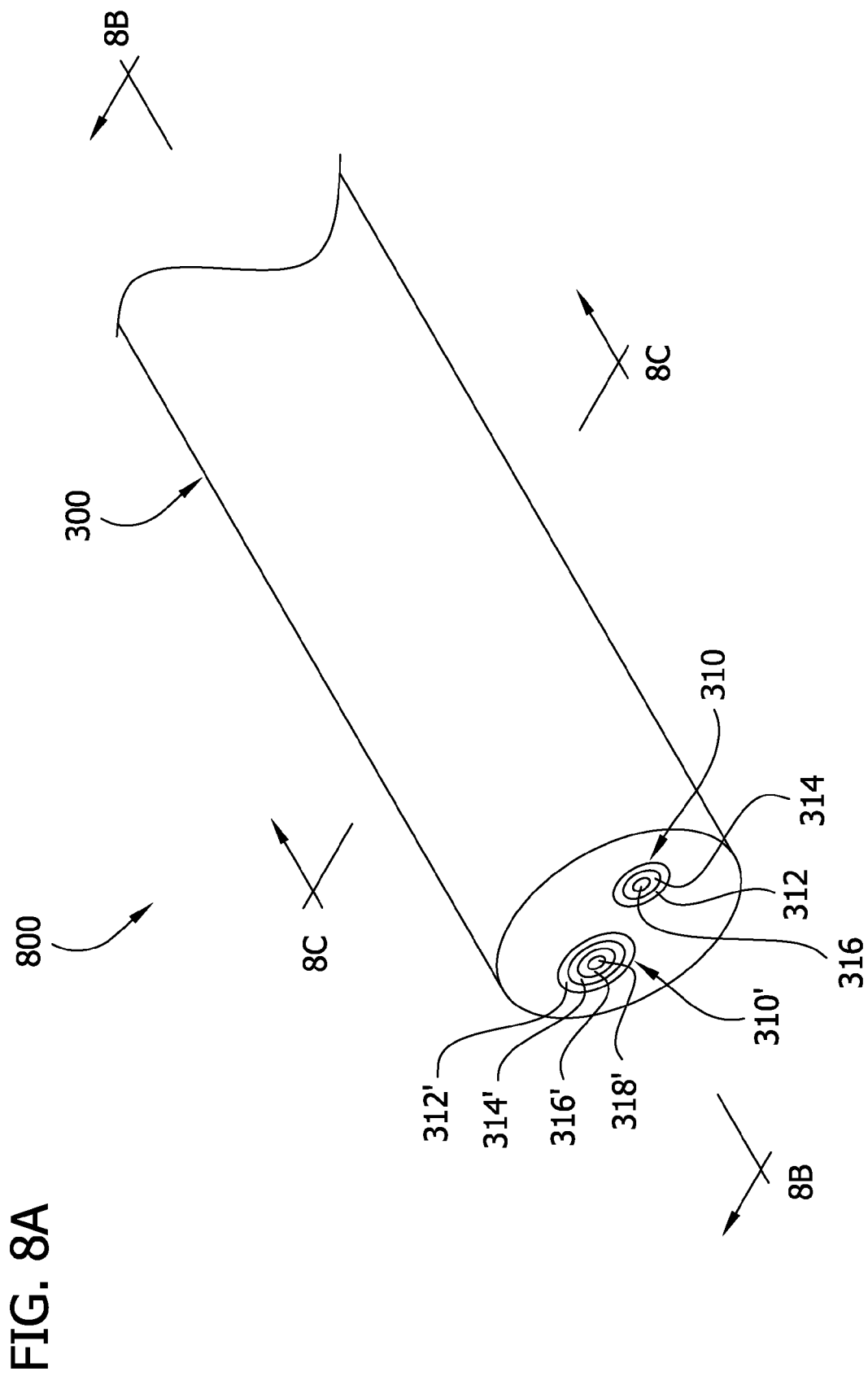
FIG. 8A is a perspective view of a conductive polymer conductor according to other aspects of this invention.
Figure 8C:
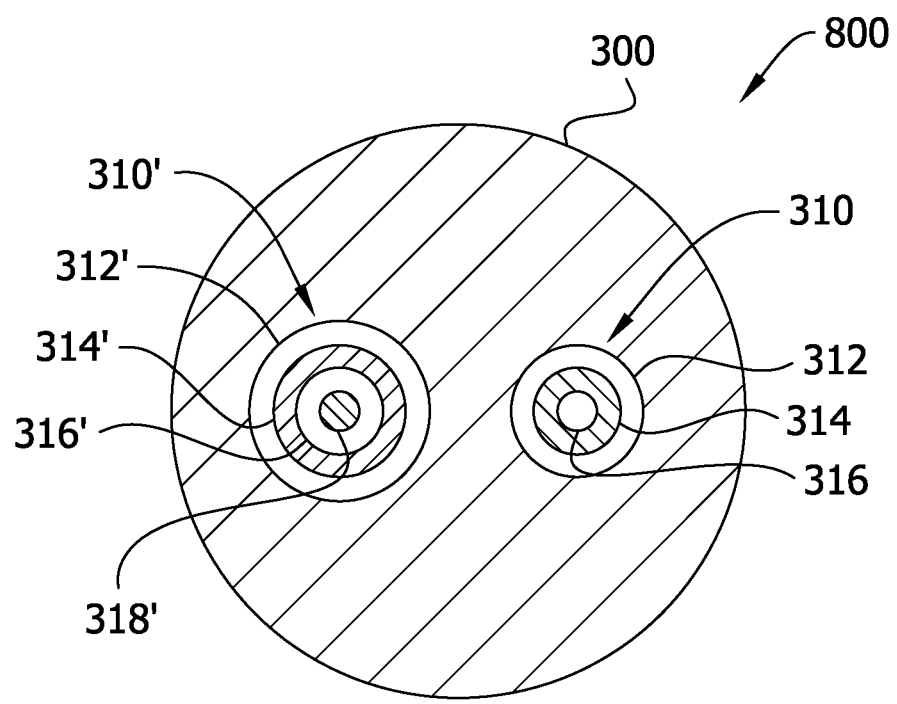
FIG. 8C is a section taken in plane 8C-8C of FIG. 8A.

In a variation of the embodiment of FIGS. 6A-D, a conductive polymer conductor having parallel arrangement of a conductive element 700 according to aspects of the invention is illustrated in FIG. 7A-C, where two parallel conductive polymer components or layers 210, 220 are formed within an insulative sheath 200. Additional insulating layers other than sheath 200 may be deposited around conductive polymer layers 210, 220 without departing from the scope of the invention. A hybrid arrangement of a conductive polymer conductor combining the coaxial and parallel arrangements of the conductive elements of FIGS. 6, 7 is illustrated in FIGS. 8A-C as conductive element 800. An insulative sheath 300 has a first conductive element 310 with polymer components 312, 316 and an insulative layer 314. The second conductive element 310' may be identical to first conductive element 310, or alternatively (and as illustrated), be differently formed with multiple conductive polymer component 312', 318' and multiple insulative sheaths 314', 316'. Indeed, each individual conductive polymer component and insulative sheath can be created and arranged per any of the previously discussed embodiments without departing from the scope of the invention.

The conductive polymer composition may comprise polypyrroles, polythiophenes, polyacetylenes, polyanilines, natural or synthetic melanins, other inherently or non-inherently conductive macromolecules and polymers, derivatives thereof, as well as copolymers and homopolymers thereof. Generally, any material providing desirable properties of biocompatibility, conductivity, flexibility, tear resistance, toughness, durability and stability may be employed. It is also highly desirable that the conductive polymer composition remain in place after application (i.e., during use) and after undergoing treatment such as curing or solidification. It is within the skill in the art to select the monomers that would form such polymers.

The conductive polymer composition of polymer layer 50 or any of the conductive polymer components described herein can further comprise dopants that improve mechanical properties, electrical properties, and/or improve processability. The conductive polymer composition comprises about 30-100% (w/w) of the conductive polymer and about 0-70% (w/w) of dopant, preferably about 60-80% (w/w) of the conductive polymer and about 20-40% (w/w) of dopant based upon the total weight of the monomers and dopant(s) in the polymerization mixture before the polymerization reaction occurs. In some instances, the conductive polymer composition comprises about 90-100% (w/w) of the conductive polymer and about 0-10% (w/w) of dopant, based upon the total weight of the monomers and dopant(s) in the polymerization mixture before the polymerization reaction occurs The dopants can include, but are not limited to, metal nanoparticles such as gold or platinum, electroplated metals, carbon nanotubes, carbon fibers, graphite, other conductive polymers, photo-crosslinking agents (e.g. benzophenone, anthraquinone, nitrophenyl azide (NPA), phenyl(trifluoromethyl)diazirine (PTD), and the like), counterions such as polystyrene sulfonate or other polymeric anions, or surfactants, which can serve to increase the mechanical strength, durability and/or the electrical conductivity and/or the processability of the composition.

Insulating sheath 54 is desirably formed of a polymer comprising silicone, polyurethane, polyimide, fluorinated ethylene propylene, or polytetrafluoroethylene. Sheath 54 may be textured as a polymeric foam, a polymeric mesh, or various blends thereof. Generally, any natural or synthetic biocompatible material having the requisite insulative properties can be employed.

In the embodiments where the conductive polymer composition is formed into a conducting sleeve, several methods may be employed. These include solvent casting of solutions or suspensions containing the polymers, electrochemical deposition, chemical polymerization, UV-initiated polymerization, or chemical vapor deposition. Such methods include, for example, the oxidative chemical vapor deposition of the polymer as described in U.S. Pat. No. 7,618,680, the chemically-initiated polymerization of the polymer as described by Peramo et al., Tissue Engineering: Part A, 14(3), 423-432 (2008), the enzyme-initiated polymerization of the polymer as described in U.S. Pat. No. 5,420,237, which are incorporated herein by reference in their entirety. The resulting conductive sleeve, as best illustrated in FIGS. 2-3, is electrically conductive and mechanically compliant, so that it can flex and function with the movement of the lead.

In the embodiments where an insulating sleeve is rendered conductive by addition of the conductive polymer, in its volume and/or on its surface, the sleeve may be manufactured either by chemical or electrochemical deposition of conductive polymers into a sleeve of insulating material. The inner surface of the sleeve is made conductive by flowing the conductive polymer materials through the insulation sleeve to coat its inner surface. In some embodiments, oxidizing and permeabilizing agents are first passed through the sleeve to clean and prepare the surface for conductive polymer attachment by methods well known in the art. For example, the chemical polymerization of conductive polymers can be accomplished by exposing the insulating sleeve to the monomer form of the conductive polymer (such as ethylenedioxythiophene or its derivatives, pyrrole, etc.) and other optional precursors including dopants, to tailor the electrical properties, mechanical properties, or processability.

The monomers or precursors used in the polymerization mixture for forming the conductive polymer composition are typically present in the mixture at concentrations of 0.001% (w/v)-10% (w/v). The solvents used include water, acetone, ethanol and other alcohols, and other organic solvents. Irrespective of the component to be coated (lead, insulating sleeve, etc.), the polymerization process is initiated by exposing the polymerization mixture as described herein to chemical oxidizers such as $AuCl_3$, $FeCl_3$ or other oxidizing agents. After this step, the component is rendered conductive. Additional steps to improve electrical properties, mechanical properties or biocompatibility involve rinsing in deionized water, exposure to other organic solvents, addition of electropolymerized conductive polymers through application of electrical currents, solvent treatments, heat treatments including annealing or cooling, mechanical extrusion, or melt processing.

It is further possible and desirable to enhance conductivity and stability by electrochemically-depositing conductive polymer. Using an insulating sleeve that has been rendered conductive by the abovementioned process as an example, the now conductive sleeve is again exposed to the polymerization mixture. The sleeve is connected to a power source as a working electrode (anode) and a counter electrode is placed in the solution. Electrical charge is applied between the working electrode and counter electrode by galvanostatic means, potentiostatic means, or by cycling the voltage from approximately 0.4-1.2V. The electrical charge initiates polymerization of the conductive polymer onto the previously deposited chemically-initiated conductive polymer elements. These steps alter the microstructure, amount of conductive polymer, or chemical composition of the sleeve and thus the resulting macroscale properties, including conductivity, mechanical strength, durability, or flexibility.

As further variations to the fabrication (and ultimately) to the final conductive polymer composition, the reagents for the polymerization reaction can be varied by using different solvents such as water, ethanol, dichloromethane, dimethyl sulfoxide, or acetone, and different oxidizing chemicals such as known strong oxidizers including iron chloride, lithium perchlorate, and ammonium perchlorate. Other metal ion solutions instead of $AuCl_3$ could be used, such as iridium tetrachloride ($IrCl_4$) or platinum chloride ($PtCl_4$). The resulting conductive polymer composition can also be further varied by using different anions, polyanions, or surfactants. In addition various other materials and chemicals can be added to the polymerization mixture or placed on the tubing itself to impart a new property or improve a specific material/physical property/characteristic: e.g. mechanical robustness/durability, pliability/flexibility, electrical or ionic conductivity, or bio-functionality. This could include but is not limited to rubbers-elastomers, carbon nanotubes, polyelectrolyte membranes or monolayers, solid electrolytes, carbon fiber or graphite particles, polymer, metal and magnetic nanoparticles, ceramics, crystalline oxides such as zinc oxide, and small molecule organic electronics such as pentacene or rubrene.

In some embodiments only certain portions of the insulating sleeve may be exposed to chemical reagents in order to restrict deposition of the conductive polymer composition. Masking of certain areas of the sleeve with photoresist, adhesive films, removable polymers, and other temporary materials may also be used to prevent non-specific deposition and to create structures including but not limited to tissue-contacting electrodes, medical device connection sites, circuits, branches, drug delivery sites, multi-channel leads and sensors. Multiple layers of conductive polymers may be applied for some of the aforementioned embodiments.

Coaxial polymer-based leads can be created by applying an additional layer of conductive polymer and insulation materials around the existing sleeve. Depending on the number of channels required, it is possible to build up successive layers of concentric conductive sleeves. Using the aforementioned masking methods, the deposition may also be restricted to portions of the sleeve to create multiple channels within a single layer of the conductive sleeve.

When forming an implantable lead having the conductive polymer composition suspended in a thermosetting polymer such as an epoxy applied to a connection thereof as described above for certain embodiments, the material can include polymer or polymer forming compounds such as polyurethane, silicone, epoxy, PEEK (poly ether ether ketone), acrylic, cyanoacrylate, epoxides, polyester, vinyl ester. The polymer can be formed either before or after application of the epoxy through any of the polymerization methods described above (e.g., initiated by hardeners such as polyamine monomers, or by various chemical, electrochemical, CVD, UV, vapor deposition methods). The material is placed at the connection to mechanically support and distribute stresses at the connection and to electrically connect the two components of the lead.

In a preferred embodiment, the conductive coating or the conductive sleeve has a thickness ranging from about 0.5 to about 1,000 μm, preferably from about 5 to about 500 μm, and more preferably from about 20 to about 100 μm. Alternatively, the insulating sleeve can be impregnated with the conductive polymer composition such that the thickness of the wall of the coated insulating sleeve ranges from about 0.5 to about 1,000 μm, preferably from about 5 to about 500 μm, and more preferably from about 20 to about 100 μm.

As used in certain embodiments, a section of shrink-wrap or non-shrink wrap tubing (silicone, silastic rubber, polyurethane, polyimide, polyolefin or other biocompatible polymer) is prepared for conductive polymer deposition by first exposing the wrap tubing or portions thereof to a solution containing oxidizing chemicals such as $FeCl_3$, $AuCl_3$, or others as well as strong acids such as HCl, $H_2SO_4$ or others, and $H_2O_2$, ozone, hydrazine, or other oxidizing species. The concentration of oxidizing agents in the solution can range from 0.1-10% (w/v). The materials are then incubated in the oxidizing solution for 1-60 minutes. The tubing is then soaked for 1-60 minutes in an aqueous monomer reagent solution made with deionized water, acetone, dichloromethane, or other organic solvent containing the monomer (ethylene dioxythiophene (EDOT), pyrrole, derivatives thereof or other conductive polymer precursor), a single dopant or a plurality of dopants such as poly(styrenesulfonate) (PSS), polyacrylamide, polyacrylate, carbon nanotubes, biological or natural surfactants, carbon fiber, polymeric fibers, naturally occurring fibers, etc. The final pH of the solution can range from acidic to basic. In some cases, portions of the tubing may be masked so that only certain portions are exposed to the precursor reagents or oxidizing agents. Some of the chemicals may be exposed only to the inner or outer portion of the tubing in order to direct deposition of the materials. The tube can then be rinsed one or more times in deionized water or organic solvent to remove excess reagents. The tube is then exposed to an oxidizing solution with the components previously described, for 1-60 minutes.

The conductive polymer forms on the surface of the insulating tube and penetrates the polymer matrix of the tube. Depending on the materials used, this may be observable by watching the insulating tubing transform in color, from essentially transparent or white to a fully dense, dark black opaque material for example. The materials are then rinsed in an appropriate solvent (deionized water, alcohol, or other organic solvent) prior to use. This final rinse may last between minutes to days. In some instances the materials are degassed in a vacuum for several hours prior to use.

Additionally the fabrication process can take place in the matrix portion (e.g. epoxide) of a liquid epoxy so that upon later formation of epoxy materials by addition of initiator/hardener (eg., polyamine), the conductive polymer extends throughout the epoxy. With such an approach, the epoxy can be prepared by mixing the epoxide component with the hardener and then the epoxy can be applied to crucial joints or connections before the epoxy has fully set.

The conductive tubing is then placed around a conductor of the lead (such as a coil, cable, or wire). Heat may be applied for the shrinkwrap process to occur. Alternatively, with non-shrinkwrap tubing, the conductor may be forced through the lumen of the conductive tubing. Depending on materials used, the conductive tubing may be compressible. In this case the conductor wire/cable/coil is inserted through the lumen of the compressible tubing that is now conductive through the aforementioned process. An exterior shrink wrap tubing is applied to the compressive conductive tubing and the conductor wire/cable/coil, and then heat is applied to compress the concentric layers together.

The conducting tubing may be used alone or in layers to provide all-polymer conductive leads. In this case the tubing is made conductive through the aforementioned process, but instead of wire/coil/cable inserted within, the tubing is used alone, in concentric layers, or side by side within another insulating tubing or housing.

Figure 9A:
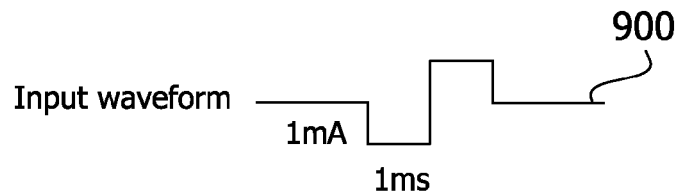
FIG. 9A is a schematic of a sample input waveform to an implantable medical lead of this invention.
Figure 9B:
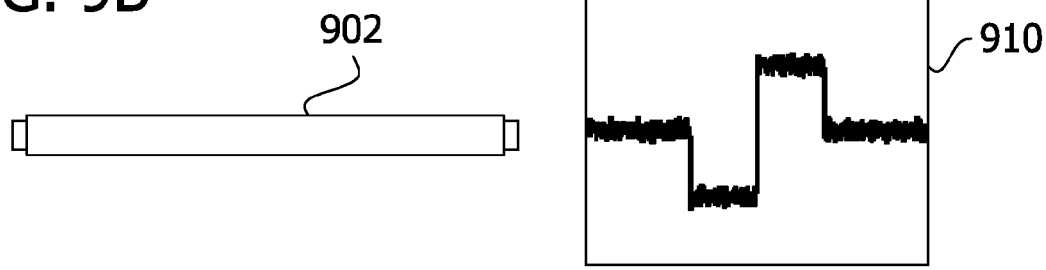
FIG. 9B is a schematic of an intact conventional medical lead or conductor and an output waveform generated by in response to the input waveform of FIG. 9A.
Figure 9C:
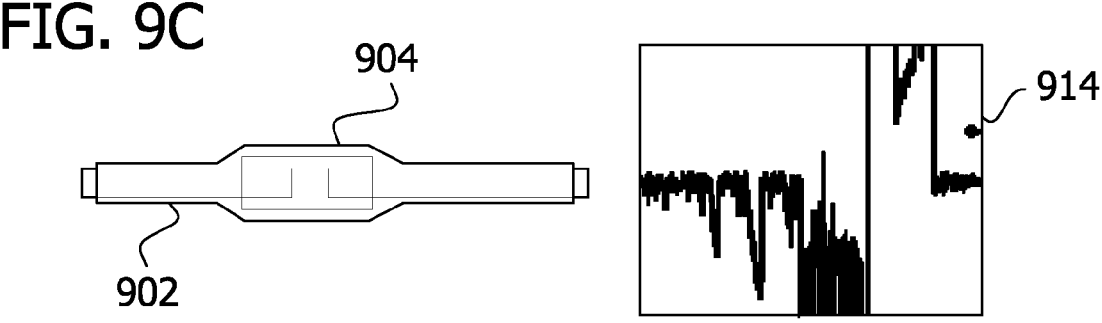
FIG. 9C is a schematic of a fractured conventional medical lead or conductor and an output waveform generated in response to the input waveform of FIG. 9A.

FIGS. 9A-D illustrate how, during regular use, a sense electrode is used to monitor activity in the body. A pace electrode of a cardiac pacemaker is used to deliver pacing signals such as the input waveform 900 shown in FIG. 9A. An unfractured lead 902 transmits the signal 900 without distortion or loss as seen in the output waveform 910 of FIG. 9B. If a conventional lead as known in the art is fractured as shown in FIG. 9C, the resulting waveform 914 is distorted due to non-conductivity of an insulating sleeve 904, and the waveform 914 does not accurately reflect the input waveform 900. When a conductive sleeve or coating 906 is applied to the fractured lead 902 per aspects of the invention (see FIG. 9D), the input waveform 900 is transmitted around the fractured segment through the conducting sleeve or coating 906. The resulting waveform 916 is very similar to the waveform 910 transmitted by the unfractured lead.

The conductive polymer or all polymer lead of certain embodiments of this invention can be used for the same applications as traditional biomedical leads, such as to connect a pulse generator with electrodes implanted in the target tissue. The all polymer lead confers certain advantages over traditional leads that contain metallic conductors. In particular, all polymer leads have much lower susceptibility to electro-magnetic radiation and will thus have less interference from sources such as microwaves, MRIs, cell phones, metal detectors, etc. All polymer leads will also have increased mechanical pliability compared to their traditional counterparts, and can thus be subjected to increased ranges of mechanical stress, strain, and loading. In another embodiment, the conductive polymer composition can be on a strand of insulating tubing, and two such strands can be within the lumen of an outer insulating tube; the outer tube can include a small hollow gap within the lumen to provide crush resistance.

Having described the invention in detail, it will be apparent that modifications and variations are possible without departing from the scope of the invention.

Figure 10B:
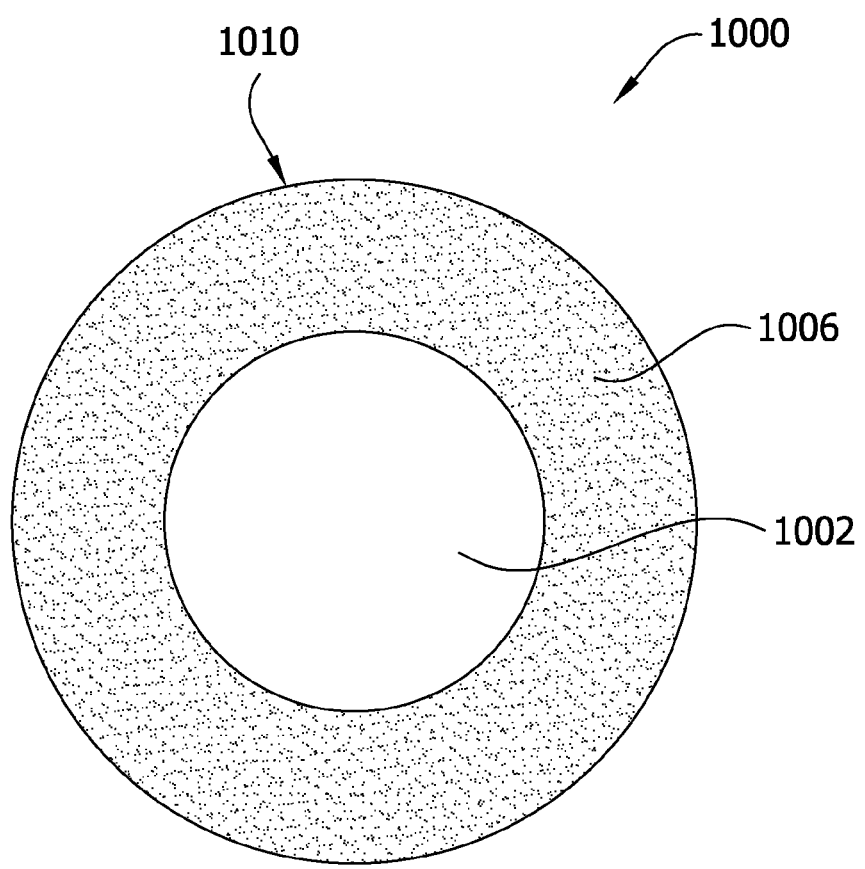
FIG. 10B is a section taken in the plane 10B-10B of FIG. 10A.

FIGS. 10A-B illustrate an additional or alternative embodiment of lead design 1000 comprising a lead component 1002

(such as metallic conductor 26 of FIG. 2) encapsulated in an insulating sheath 1006. A conductive polymer deposit 1010 permeates the insulating sheath 1006 to expose an electrical connection between the surface of the insulating sheath and the encapsulated lead component 1002.

In general, polymer deposit 1010 may be formed on any length along the total length of the sheath 1006, cover any amount of surface area of the total surface area exposed by the sheath, penetrate the insulating sheath to any possible depth (including the total thickness of the sheath), and/or have any desirable cross section other than illustrated in FIG. 10B. The fabrication methods discussed earlier and in various examples presented below are operable for such variable design. Further, any number of such conductive polymer deposits, of identical or disparate shape, may be created in insulating sheath 1006.

Figure 11B:
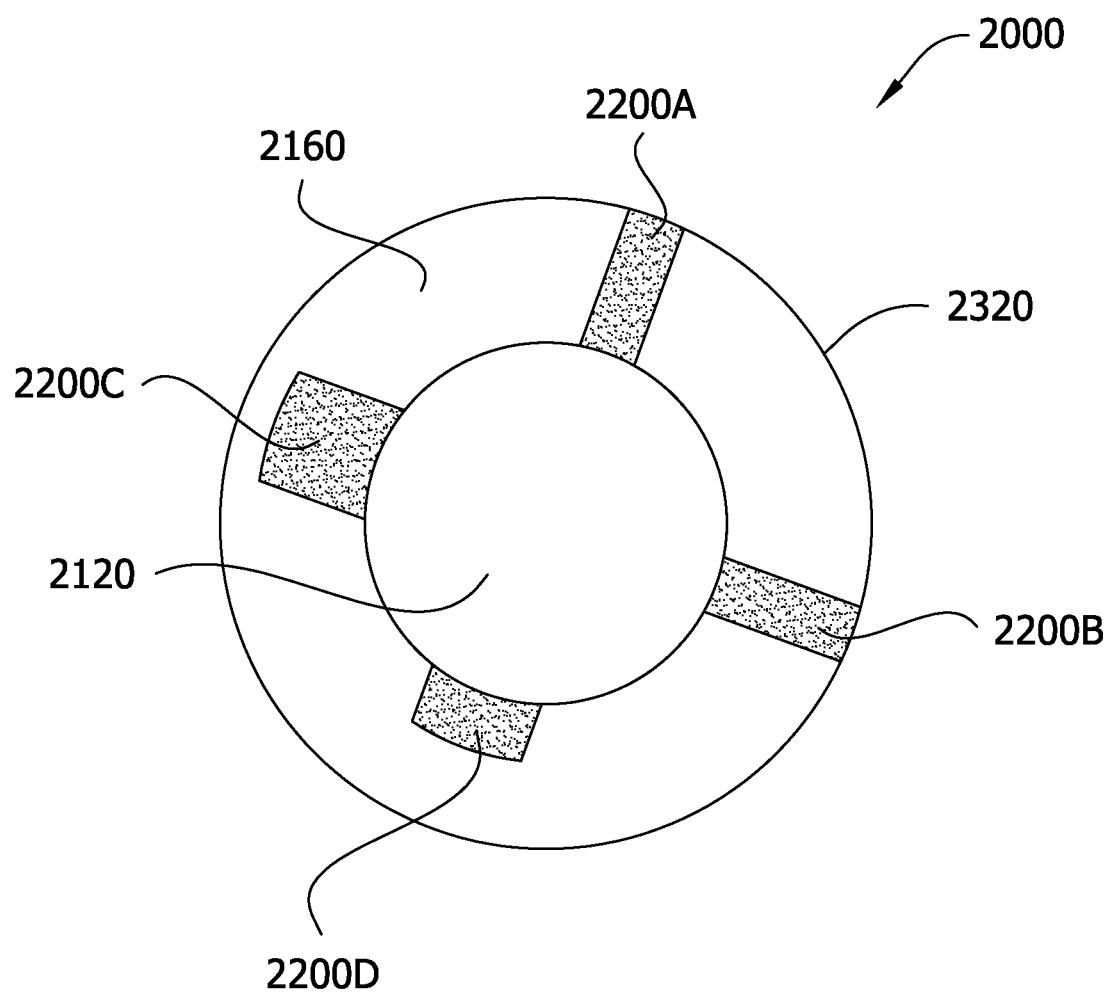
FIG. 11B is a section taken in the plane 11B-11B of FIG. 11A.

FIGS. 11A-B illustrate an exemplary and non-limiting embodiment of lead design 2000 where a conductive core 2120 is surrounded by an insulating sheath 2160. Sheath 2160 has multiple conductive polymer deposits 2200A-D formed therein. Notably, polymer deposits 2200A-B provide both end and surface connectivity (from the surface 2320 of the insulating sheath) to the conductive core 2120, while polymer deposits 2200C-D do not permeate the entire thickness of sheath 2160, and are usable for end connectivity at end 2300 alone. Alternatively, core 2120 may be insulative.

Figure 12B:
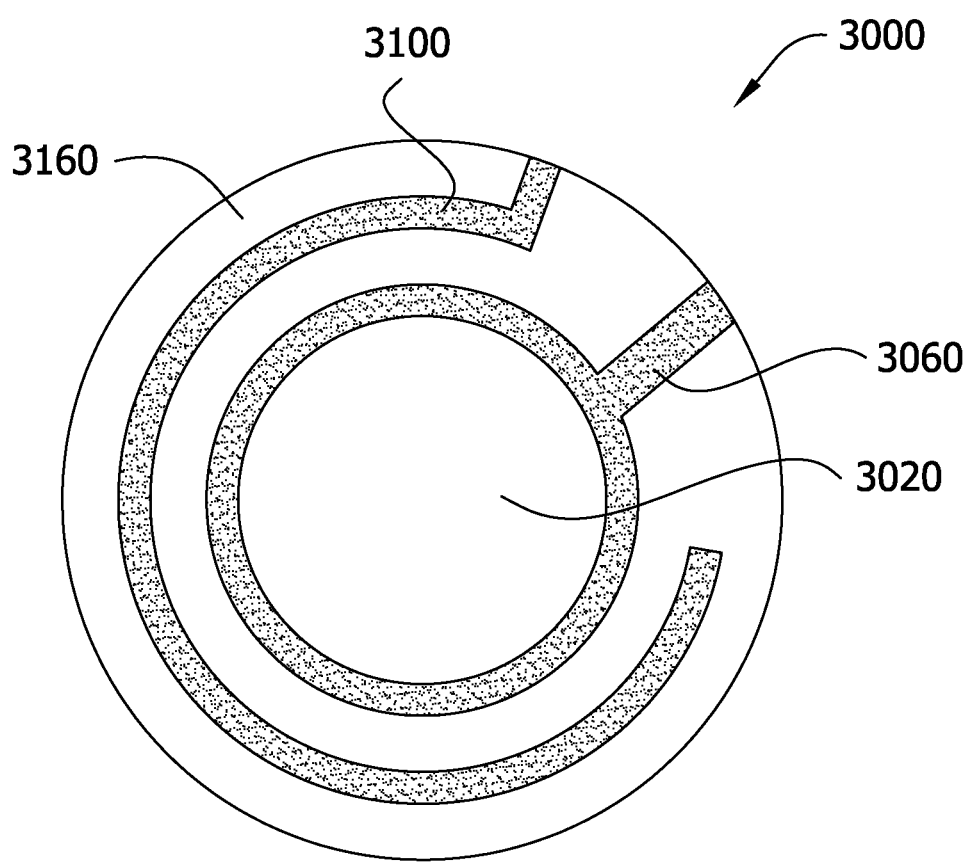
FIG. 12B is a section taken in the plane 12B-12B of FIG. 12A.

FIGS. 12A-B illustrate a lead design 3000 where an insulative core 3020 is surrounded by an insulative sheath 3160 having conductive polymer deposits 3060 and 3100 formed therein. The inner polymer deposit 3060 completely encircles core 3020 and is exposed on part of surface 3140 of sheath 3160 as illustrated. Outer polymer deposit 3100, formed along the entire length of the sheath 3160, is exposed to surface 3140 as well, and is further shaped to permit electrical isolation from the polymer deposit 3060.

As described in detail earlier, any of the polymer deposits of FIGS. 10-12 may be formed by several means, including as a conductive coating, a permeation or deposit of the conductive polymer composition into the insulating sheath, and so on.

The following non-limiting examples are provided to further illustrate the present invention.

EXAMPLE 1

Formation of Conductive Sleeve

A section of silicone rubber or polyethylene tubing was first soaked for 15 minutes in an aqueous monomer reagent bath (the polymerization mixture) containing 0.1% (w/v) ethylene dioxythiophene monomer (EDOT) and 0.2% (w/v) polystyrene sulfonate dopant in deionized water (pH of about 4.2 at room temperature). The tubing was then rinsed several times in deionized water to remove excess monomer and the inner lumen was cleared of monomer solution by blowing air through the tube. The EDOT-absorbed tubing was then placed in an aqueous reaction bath of 0.5-1% gold chloride ($AuCl_3$) solution for 10 minutes. A chemical polymerization reaction then occurred immediately in which the conductive polymer PEDOT (Poly(3,4-ethylenedioxythiophene)) was formed from the EDOT monomer, with a polyanion dopant and gold nanoparticles being incorporated directly into the resulting conductive polymer composite material. The PEDOT composite material formed on the surface of the tube and penetrated the polymer matrix of the silicone or polyethylene tube material as evidenced by the tubing transforming from essentially transparent or white to a fully dense, dark black opaque material. The PEDOT composite material-coated tube was allowed to dry at room temperature, including drying of the inner lumen.

EXAMPLE 2

Use of Conductive Sleeve to Repair a Fractured Wire

Figure 9D:
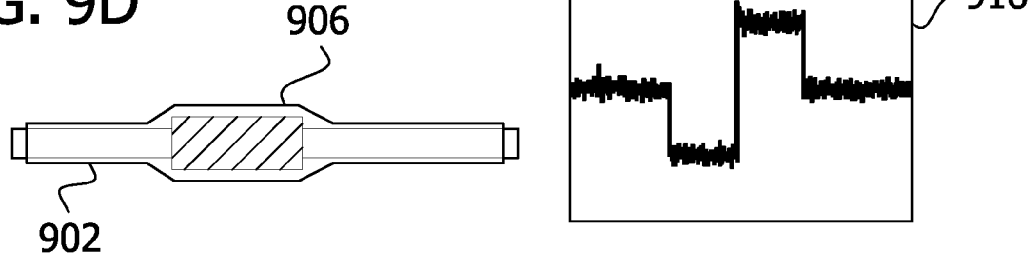
FIG. 9D is a schematic of a fractured medical lead or conductor of this invention and an output waveform generated in response to the input waveform of FIG. 9A.

The PEDOT composite material-coated tube ("PEDOT tube") of Example 1 was placed around a section of Teflon-insulated platinum wire that was cut in half at the center. The PEDOT tube was placed around the cut/break in the wire such that the wire fit snugly within the lumen of the PEDOT tube and the broken ends of the wire were in contact with the PEDOT coating. The PEDOT tube essentially formed a conductive sleeve around the wire break. The PEDOT tube was then placed within the lumen of an electrically-insulating heat-shrink polyolefin tube and the heat-shrink tube was heat-activated using a blow dryer until the insulating heat shrink tube tightly hugged and stabilized the system assuring that the PEDOT sleeve-covered broken wire assembly was stable and the broken wire remained in contact with the conductive PEDOT tube. Then an electrical pulse similar to what a biomedical device would experience was sent through the wire assembly which was attached to a circuit with the input device being a current pulse signal generator and the output device being an oscilloscope. With the conductive PEDOT tube, the wire was able to complete the circuit and the pulse was detected by the oscilloscope. The PEDOT tube acted as a bridge or fail-safe allowing the electrical pulse to be transmitted through the circuit despite the break or crack in the wire. This assembly is shown in FIG. 9D and is labelled "Fractured wire—with BT DOT sleeve." Note that a pacing signal applied through such a fractured wire would result in a waveform similar to or substantially the same as the waveform provided by the same wire when unfractured as shown in FIG. 9B.

In a comparative example, a section of the Teflon-insulated platinum wire was cut in half at the center. The electrically-insulating heat-shrink polyolefin tube was placed around the cut/break in the wire such that the wire fit snugly within the lumen of the heat-shrink tube. Then an electrical pulse similar to what a biomedical device would experience was sent through the wire assembly which was attached to a circuit with the input device being a current pulse signal generator and the output device being an oscilloscope. The oscilloscope did not receive any information because the electrical pulse was not able to complete the circuit, resulting in a short. This assembly is shown in FIG. 9C and is labeled "Fractured wire—with non-conductive sleeve." Note that a pacing signal applied through such a fractured wire would result in a waveform unlike the waveform provided by the same wire when unfractured.

EXAMPLE 3

Formation of Polymer Tubing with Conductive Inner Lumen

To isolate the inner lumen, a section of polyurethane or silicone tubing was connected to the needle of a syringe that was in turn mounted in a syringe pump. An oxidizing solution containing 3 parts concentrated sulfuric acid and one part 30% hydrogen peroxide was then pumped through the tubing for 10 minutes. The syringe was then flushed with deionized water for 5 minutes and then 3% aminopropyltrimethoxysilane in ethanol for 5 minutes and then again with deionized water for 5 minutes before introduction of the polymerization mixture. The polymerization mixture containing 0.1% (w/v) ethylenedioxythiophene in deionized water was pumped through the tubing for 15 minutes. The tube was then flushed with deionized water for 2 minutes in order to remove any residual monomer. To cause polymerization of the conductive polymer, the oxidizing solution comprised of 0.5-1.0% gold chloride in deionized water at pH of 2.5 was pumped through the tubing for 10 minutes. The tube was then flushed with deionized water for 15 minutes to remove any residual reagents. The conductive polymer was thereby formed on the inner surface of the tubing. The conductive polymer was dark in color and thus by sectioning the tubing it could be seen that the conductive polymer also extended into the tubing for a distance of approximately 50-100 um, but did not extend to the outer surface of the tubing. The tubing can now be applied to the metallic wire and coiled for use in a medical device lead.

EXAMPLE 4

Coaxial all Polymer Lead

A multi-channel all-polymer lead can be fabricated by following the steps in example 3 to create the polymer tubing with a conductive inner lumen. In certain embodiments, the conductive polymer deposition process could also be applied with the tube sealed at either end so that conductive polymer is deposited solely on the outer surface of the tubing. A section of this tubing is then inserted into another section of this tubing to create a coaxial all polymer lead. Using tubing of increasingly larger diameters, it is possible to create a multi-layered coaxial lead. Alternatively, layers of fully-conductive tubing can be alternated with insulating tubing to create the coaxial structure.

EXAMPLE 5

Patterned Polymer Lead and Electrode

In order to restrict the deposition of conductive polymer to certain portions of the lead, masking can be performed. To make longitudinal conductive pathways that do not extend around the full circumference of the tubing, either end of a polyurethane or silastic tubing is plugged to prevent coating of the inner lumen. The tubing is then masked such that only the lower half of the fiber is exposed either through a slit or with a panel. Next, the polymerization mixture is sprayed onto the tubing and left to adsorb for 15 minutes. The tubing is then processed as in Example 1. More complex patterning can be performed using extrusion, ink-jet printing, complex masking and spraying, and painting or spraying on removable masks onto the tubing. Contact sites, electrodes, or interconnects with different geometries, textures, penetration depths, or materials properties for connection with devices or tissue can be made.

EXAMPLE 6

Extruded Biomedical Tubing with Conductive Polymer

Tubing for medical leads can be made by extrusion from melts or solutions of the insulating or support polymers mixed with the conductive monomer or precursors for the conductive polymer. The polymer and precursor mixture is forced through a small die or tip and is typically collected on a spinning mandrel or other receptacle. Polymerization is carried out either chemically, for example by exposing the ejected polymer mixture to an oxidizing atmosphere, or electrochemically, by applying an electrical voltage bias (~1,000V/in) between the die or tip and the collection vehicle. The resulting tubing is conductive throughout. Alternatively, multilayer coextrusion can be used to produce tubing with conductive layers or traces.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. An implantable medical lead comprising:
   a conducting electrode comprising:
      a proximal end;
      a distal end;
   a conductive polymer connected to provide an electrically conductive path from the proximal end to the distal end;
   an insulating sheath surrounding the conductive polymer to electrically insulate a surface of the conductive polymer;
   a second conducting electrode comprising a second conductive polymer positioned along the insulating sheath;
   a second insulating sheath surrounding the second conductive polymer to electrically insulate a surface of the second conductive polymer,
   wherein either: (a) the conductive polymer penetrates the insulating sheath to a depth that is equal to or less than the wall thickness of the insulating sheath; (b) the conductive polymer penetrates a length equal to or less than a total length of the insulating sheath; or (c) the conductive polymer penetrates a surface area equal to or less than a total surface area of the insulating sheath.

2. The implantable medical lead of claim 1, wherein the conductive polymer further comprises a dopant.

3. The implantable medical lead of claim 2, wherein the conductive polymer is a reaction product of a polymerization mixture comprising about 30-100% (w/w) of conducting monomer, and 0-70% (w/w) of the dopant based on the total weight of the conducting monomer and the dopant in the polymerization mixture.

4. The implantable medical lead of claim 2, wherein the conductive polymer is a reaction product of a polymerization mixture comprising about 60-80% (w/w) of conducting monomer, and 20-40% (w/w) of the dopant based on the total weight of the conducting monomer and the dopant in the polymerization mixture.

5. The implantable medical lead of claim 2, wherein the conductive polymer is a reaction product of a polymerization mixture comprising about 90-100% (w/w) of conducting monomer, and 0-10% (w/w) of the dopant based on the total weight of the conducting monomer and the dopant in the polymerization mixture.

6. The implantable medical lead of claim 2, wherein the dopant comprises one or more of the following electrical dopants to impart conductivity: metal particles, metal nanoparticles, electroplated metals, carbon nanotubes, carbon fibers, graphite, an anionic molecule, a salt, a non-polymeric conductive macromolecule, or a polymeric anion.

7. The implantable medical lead of claim 2, wherein the dopant comprises one or more of the following mechanical dopants to improve mechanical strength of the conductive polymer: polystyrene sulfonate (PSS), polyacrylamide, polyacrylate, carbon fibers, carbon nanotubes, a copolymer with anionic segments, or a crosslinking agent.

8. The implantable medical lead of claim 2, wherein the dopant comprises one or more of the following deposition facilitator dopants to improve processability of the conductive polymer: a counterion, a surfactant, a photo-initiator, an oxidizing agent, a polymeric anion, or a copolymer with anionic segments.

9. A method of making the implantable medical lead of claim 2, the method comprising:
exposing a surface of the insulating sheath to a polymerization mixture and an oxidizing agent polymerization initiator to form the conductive polymer on the surface of the insulating sheath, the polymerization mixture containing a conducting monomer and the dopant;
connecting the conductive polymer to the distal end and the proximal end of the conducting electrode to form the electrically conductive path.

10. The method of claim 9, further comprising exposing a surface of a second insulating sheath to the polymerization mixture and the oxidizing agent polymerization initiator to form a second conductive polymer on the surface of the second insulating sheath, wherein the second insulating sheath is of larger diameter than the insulating sheath; and inserting the insulating sheath into the lumen of the second insulating sheath.

11. The method of claim 10, further comprising heating the second insulating sheath after the insulating sheath is inserted into the lumen.

12. The method of claim 11, wherein the heating is annealing.

13. The method of claim 9, wherein the polymerization mixture contains the oxidizing agent polymerization initiator.

14. The method of claim 13, wherein the conducting monomer is present in the polymerization mixture in a concentration of 0.001 to 10% (w/v) based on the total weight of the mixture.

15. The method of claim 13, wherein the insulating sheath is exposed to the polymerization mixture for 1 to 60 minutes.

16. The method of claim 9, wherein the surface of the insulating sheath is exposed to the polymerization mixture before the surface is exposed to the oxidizing agent polymerization initiator.

17. The method of claim 16, wherein the insulating sheath is exposed to the oxidizing agent polymerization initiator for 1 to 60 minutes.

18. The method of claim 9, wherein the oxidizing agent polymerization initiator is present in solution in a concentration ranging from 0.1-10% (w/v).

19. The method of claim 9, wherein the polymerization mixture comprises a solvent, and the solvent comprises water or an organic solvent.

20. The method of claim 19, wherein the organic solvent comprises acetone, an alcohol, dimethyl sulfoxide, or dichloromethane.

21. The method of claim 9, wherein the conducting monomer comprises one or more of, thiophene, ethylenedioxythiophene (EDOT), aniline, a natural or synthetic melanin, or a derivative thereof.

22. The method of claim 9, wherein the insulating sheath is a film, foam, sheet, mesh, or fabric made of one or more of the following insulating materials: silicone, polyurethane, polyimide, ethylene tetrafluoroethylene, polytetrafluoroethylene, poly ether ether ketone, or polyolefin.

23. The implantable medical lead of claim 1, wherein the insulating sheath is a film, foam, sheet, mesh, or fabric made of one or more of the following insulating materials: silicone, polyurethane, polyimide, ethylene tetrafluoroethylene, polytetrafluoroethylene, poly ether ether ketone, or polyolefin.

24. The implantable medical lead of claim 1, wherein the electrical connections are soldered, welded, pressure fitted, or crimped connections.

25. The implantable medical lead of claim 1, wherein the conductive polymer comprises one or more electrical dopants, mechanical dopants, or processability dopants.

26. The implantable medical lead of claim 1, wherein one or more of the conductive polymer and the insulating sheath is modified by exposure to oxidizing chemicals, acids, or a combination thereof to impart one or more of the following properties: wettability, permeability, porosity, adhesion, or texture.

27. The implantable medical lead of claim 1, wherein one or more of the conductive polymer and the insulating sheath is modified by exposure to a silane, a self-assembled monolayer, or a combination thereof to impart one or more of the following surface properties: wettability, permeability, porosity, adhesion, or texture.

28. The implantable medical lead of claim 1, wherein the conductive polymer penetrates the insulating sheath to a depth that is equal to or less than the wall thickness of the insulating sheath.

29. The implantable medical lead of claim 1, wherein the conductive polymer penetrates a length equal to or less than a total length of the insulating sheath.

30. The implantable medical lead of claim 1, wherein the conductive polymer penetrates a surface area equal to or less than a total surface area of the insulating sheath.

31. The implantable medical lead of claim 1 wherein the insulating sheath and the second insulating sheath further comprise coaxial sheaths.

32. The implantable medical lead of claim 1 wherein the conductive polymer is positioned along and insulated from the second conductive polymer inside the implantable medical lead.

33. The implantable medical lead of claim 1 wherein the conductive polymer comprises one or more of the following conducting materials: polypyrrole, polythiophene, polyethylenedioxythiophene (PEDOT), polyaniline, polyacetylene, natural or synthetic melanins, or a derivative, copolymer or homopolymer thereof.

34. The implantable medical lead of claim 33 wherein the conductive polymer comprises one or more of the following conducting materials: polythiophene, polyethylenedioxythiophene (PEDOT), polyaniline, natural or synthetic melanins, or a derivative, copolymer or homopolymer thereof.

* * * * *